US011543332B2

(12) United States Patent
Molyneux et al.

(10) Patent No.: US 11,543,332 B2
(45) Date of Patent: Jan. 3, 2023

(54) SYSTEM AND METHOD FOR CHARACTERIZING, MONITORING, AND DETECTING BIOAEROSOL PRESENCE AND MOVEMENT IN AN INDOOR ENVIRONMENT

(71) Applicant: Poppy Health, Inc., Mountain View, CA (US)

(72) Inventors: Sam D. Molyneux, Mountain View, CA (US); Elizabeth Caley, Mountain View, CA (US); Daniela Bezdan, Mountain View, CA (US); Ricardo Vidal, Mountain View, CA (US); Nathan Volman, Mountain View, CA (US); Tae Joon Yi, Mountain View, CA (US); Kevin Slavin, Mountain View, CA (US)

(73) Assignee: Poppy Health, Inc., Mountain View, CA (US)

( * ) Notice: Subject to any disclaimer, the term of this patent is extended or adjusted under 35 U.S.C. 154(b) by 0 days.

(21) Appl. No.: 17/728,823

(22) Filed: Apr. 25, 2022

(65) Prior Publication Data

US 2022/0341823 A1     Oct. 27, 2022

Related U.S. Application Data

(60) Provisional application No. 63/286,821, filed on Dec. 7, 2021, provisional application No. 63/286,815, filed on
(Continued)

(51) Int. Cl.
    *G01N 1/22*   (2006.01)
(52) U.S. Cl.
    CPC ......... *G01N 1/2202* (2013.01); *G01N 1/2273* (2013.01); *G01N 2001/2223* (2013.01)

(58) Field of Classification Search
    CPC ............... G01N 1/2273; G01N 1/2208; G01N 2001/2223; G01N 1/2211;
    (Continued)

(56) References Cited

U.S. PATENT DOCUMENTS 5,421,214 A * 6/1995 Burgdorfer .......... G01N 1/2202
                                                    73/863.22
6,363,769 B2 * 4/2002 Krajewski ............... G01F 25/15
                                                    73/1.06
(Continued)

FOREIGN PATENT DOCUMENTS

CN          111662816 A      9/2020
CN          112014528 A     12/2020
(Continued)

OTHER PUBLICATIONS

W. John Kress et al., "DNA barcodes: Genes, genomics, and bioinformatics", The Proceedings of the National Academy of Sciences, vol. 105, No. 8, Feb. 26, 2008. (Year: 2008).*
(Continued)

*Primary Examiner* — David A. Rogers
(74) *Attorney, Agent, or Firm* — Run8 Patent Group, LLC; Peter Miller; Leah Raddatz

(57) ABSTRACT

One variation of a method includes, during a calibration period: triggering collection of an initial bioaerosol sample by an air sampler located in an environment; and triggering dispensation of a tracer test load by a dispenser located in the environment; accessing a detected barcode level of a barcode detected in the initial bioaerosol sample; accessing a true barcode level of the barcode contained in the tracer test load; and deriving a calibration factor for the environment based on a difference between the detected barcode level and the true barcode level. The method further includes, during a live period succeeding the calibration period: triggering collection of a first bioaerosol sample by the air sampler;
(Continued)

accessing a detected pathogen level of a pathogen detected in the first bioaerosol sample; and interpreting a predicted pathogen level of the pathogen in the environment based on the detected pathogen level and the calibration factor.

20 Claims, 8 Drawing Sheets

Related U.S. Application Data on Dec. 7, 2021, provisional application No. 63/286,806, filed on Dec. 7, 2021, provisional application No. 63/178,721, filed on Apr. 23, 2021.

(58) Field of Classification Search
CPC ....... G01N 2001/2276; G01N 15/0606; G01N 2015/0088
See application file for complete search history.

(56) References Cited

U.S. PATENT DOCUMENTS 6,974,669 B2 * 12/2005 Mirkin ................. C12Q 1/6825 435/7.1
7,389,158 B2 * 6/2008 Desrochers ........ G01N 33/0034 700/277
7,578,973 B2 8/2009 Call et al.
7,633,606 B2 12/2009 Northrup et al.
8,272,280 B2 * 9/2012 Jones, Jr. ............... A22B 5/007 73/31.02
8,539,840 B2 * 9/2013 Ariessohn ............ G01N 1/2202 73/860
8,578,796 B2 * 11/2013 Cho ..................... G01N 1/2205 73/28.01
8,689,648 B1 * 4/2014 Heff ..................... G01N 1/2273 73/863.22
9,063,040 B2 * 6/2015 Calio ....................... G01N 1/24
9,170,178 B2 * 10/2015 Sobek .................. G01N 1/2202
9,261,885 B2 * 2/2016 Tryfonos ........... G01N 33/0006
9,689,792 B1 * 6/2017 Sickenberger ......... G01N 15/14
9,989,445 B2 * 6/2018 Ligugnana ................ H02J 7/00
10,919,047 B2 * 2/2021 Mainelis ................... B03C 3/41
10,928,389 B2 * 2/2021 Fan ...................... G01N 33/582
11,300,484 B1 * 4/2022 Bango .................... G01N 23/00
11,365,409 B2 * 6/2022 Shum ................. C12N 15/1065
2006/0040286 A1 * 2/2006 Mirkin ............. G01N 33/54333 435/6.11
2011/0252897 A1 * 10/2011 Swenson .............. G01N 1/2208 73/863
2012/0174650 A1 * 7/2012 Ariessohn ............ G01N 1/2202 73/23.2
2021/0208062 A1 * 7/2021 Linden ............... G01N 21/3504
2021/0324485 A1 * 10/2021 Hodges .................. C12Q 1/701
2022/0034763 A1 * 2/2022 Dutta ................... G01N 1/2205
2022/0091010 A1 * 3/2022 Wystup .................. G01N 21/85

FOREIGN PATENT DOCUMENTS

JP 2017096727 A * 6/2017
JP 2017096727 A 6/2017
KR 20110097199 A * 8/2011
KR 20110097199 A 8/2011
WO WO-2006060872 A1 * 6/2006 ............. C12Q 1/708
WO 2019018559 A1 1/2019
WO 2022047340 A1 3/2022
WO 2022081543 A1 4/2022
WO WO-2022081543 A1 * 4/2022

OTHER PUBLICATIONS

International Search Report and Written Opinion for International Patent Application No. PCT/US2021/64875 dated Mar. 29, 2022; 13 pages.
M. Z. Bazant, J. W. Bush, A guideline to limit indoor airborne transmission of covid-19 Proceedings of the National Academy of Sciences. 118 (2021), doi:10.1073/pnas.2018995118.
Non-Final Office Action for United States U.S. Appl. No. 17/559,257 dated Jun. 8, 2022; 7 pages.

* cited by examiner

*FIGURE 2*

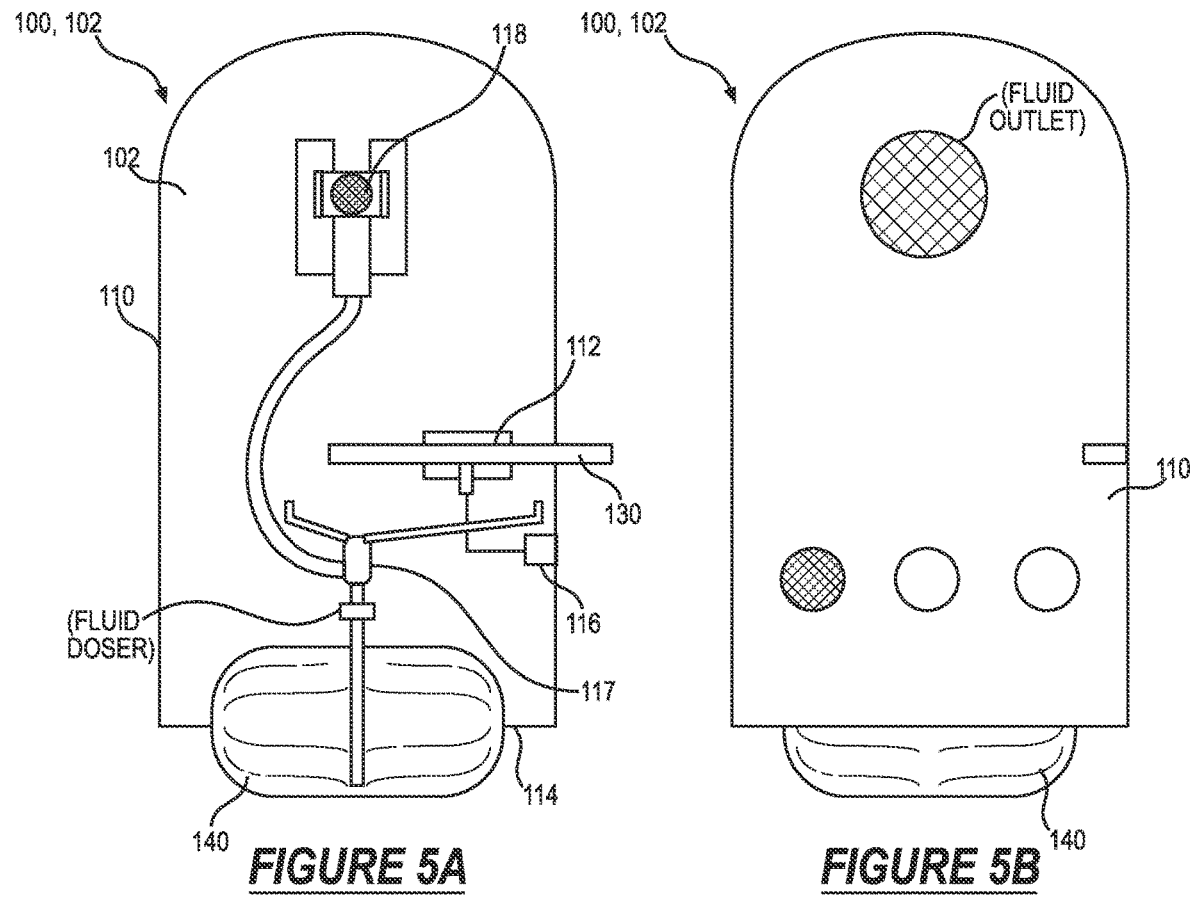
*FIGURE 5A*
*FIGURE 5B*
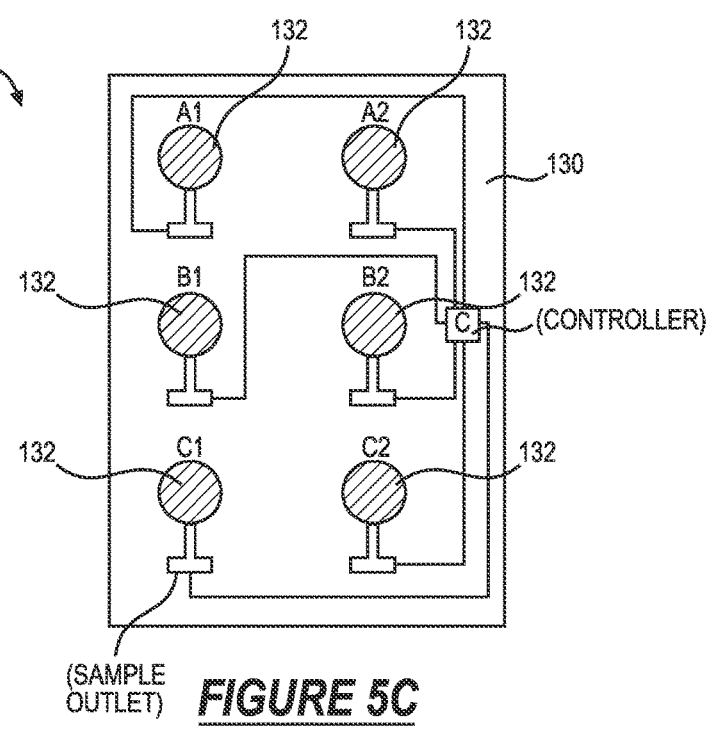
*FIGURE 5C*

SYSTEM AND METHOD FOR CHARACTERIZING, MONITORING, AND DETECTING BIOAEROSOL PRESENCE AND MOVEMENT IN AN INDOOR ENVIRONMENT

TECHNICAL FIELD

This invention relates generally to the field of metagenomics and more specifically to a new and useful method for pathogen detection in the field of metagenomics.

CROSS-REFERENCE TO RELATED APPLICATIONS

This Application claims the benefit of U.S. Provisional Application 63/286,815, filed on 7 Dec. 2021, U.S. Provisional Application 63/286,806, filed on 7 Dec. 2021, U.S. Provisional Application 63/286,821, filed on 7 Dec. 2021, and U.S. Provisional Application 63/178,721, filed on 23 Apr. 2021, each of which is incorporated in its entirety by this reference.

BRIEF DESCRIPTION OF THE FIGURES

Figure 2:
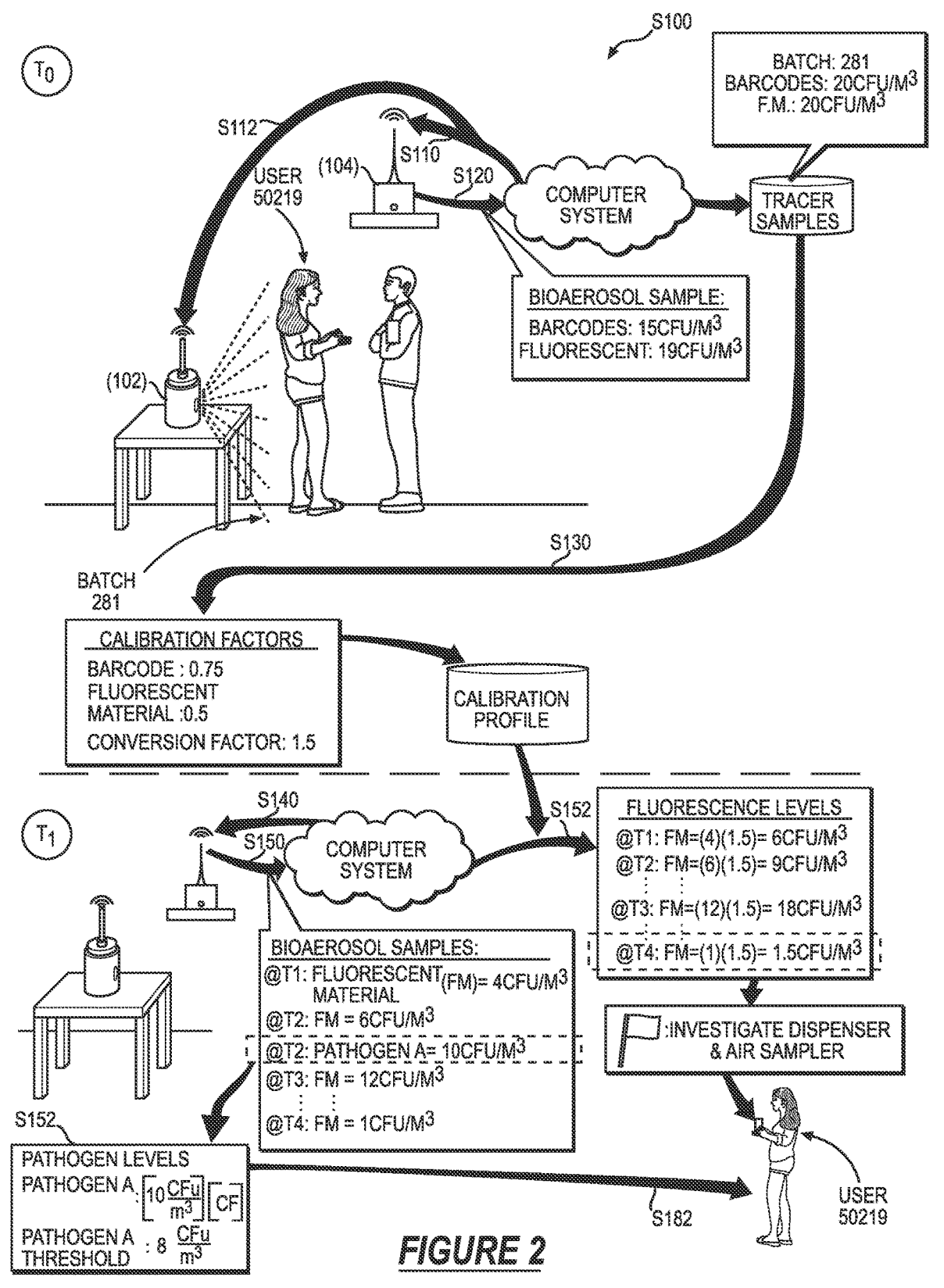

FIG. 2 is a flowchart representation of the method;
FIGS. 5A, 5B, and 5C are schematic representations of a system.

DESCRIPTION OF THE EMBODIMENTS

Figure 1:
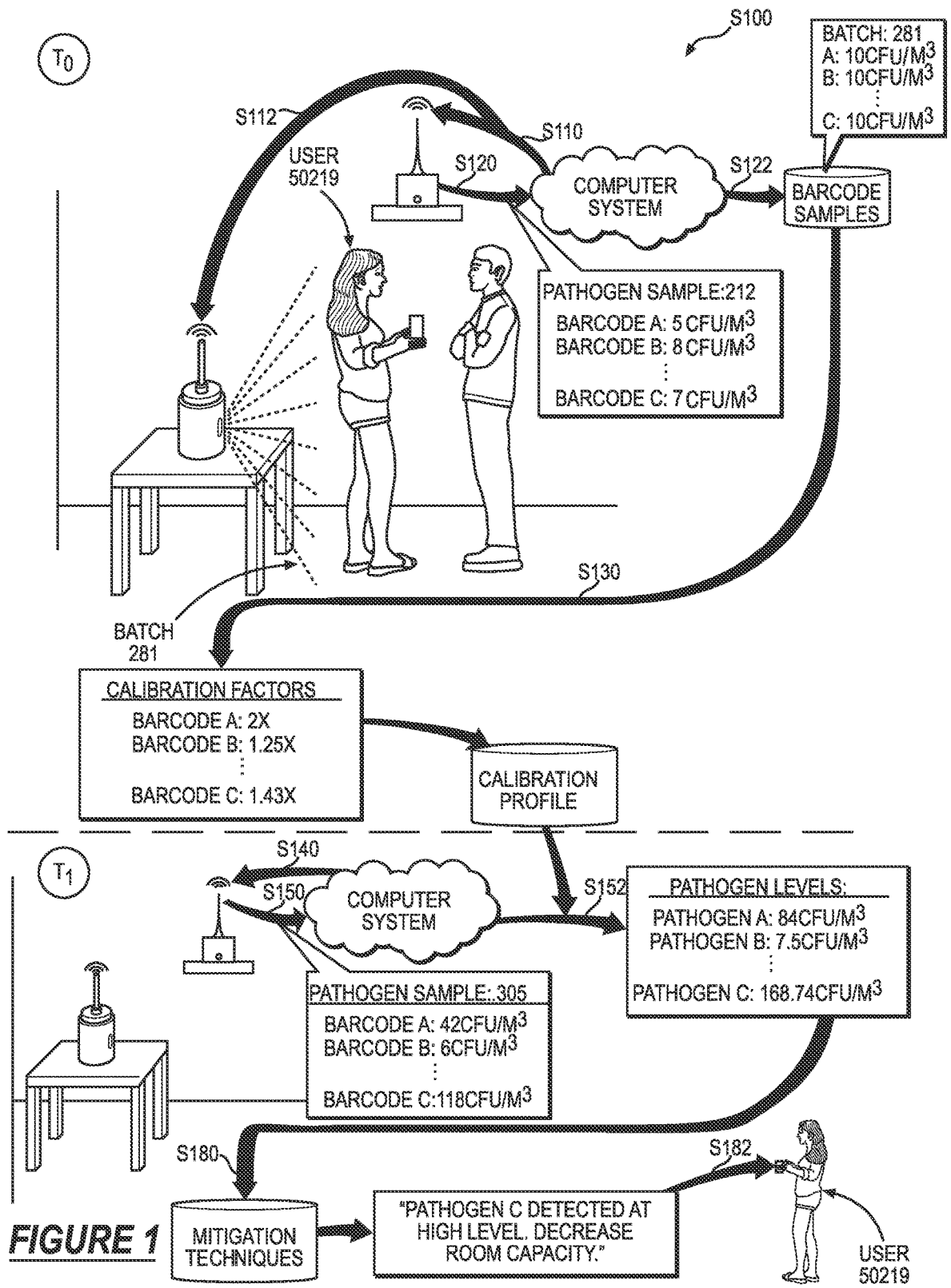
FIG. 1 is a flowchart representation of a method.
Figure 3:
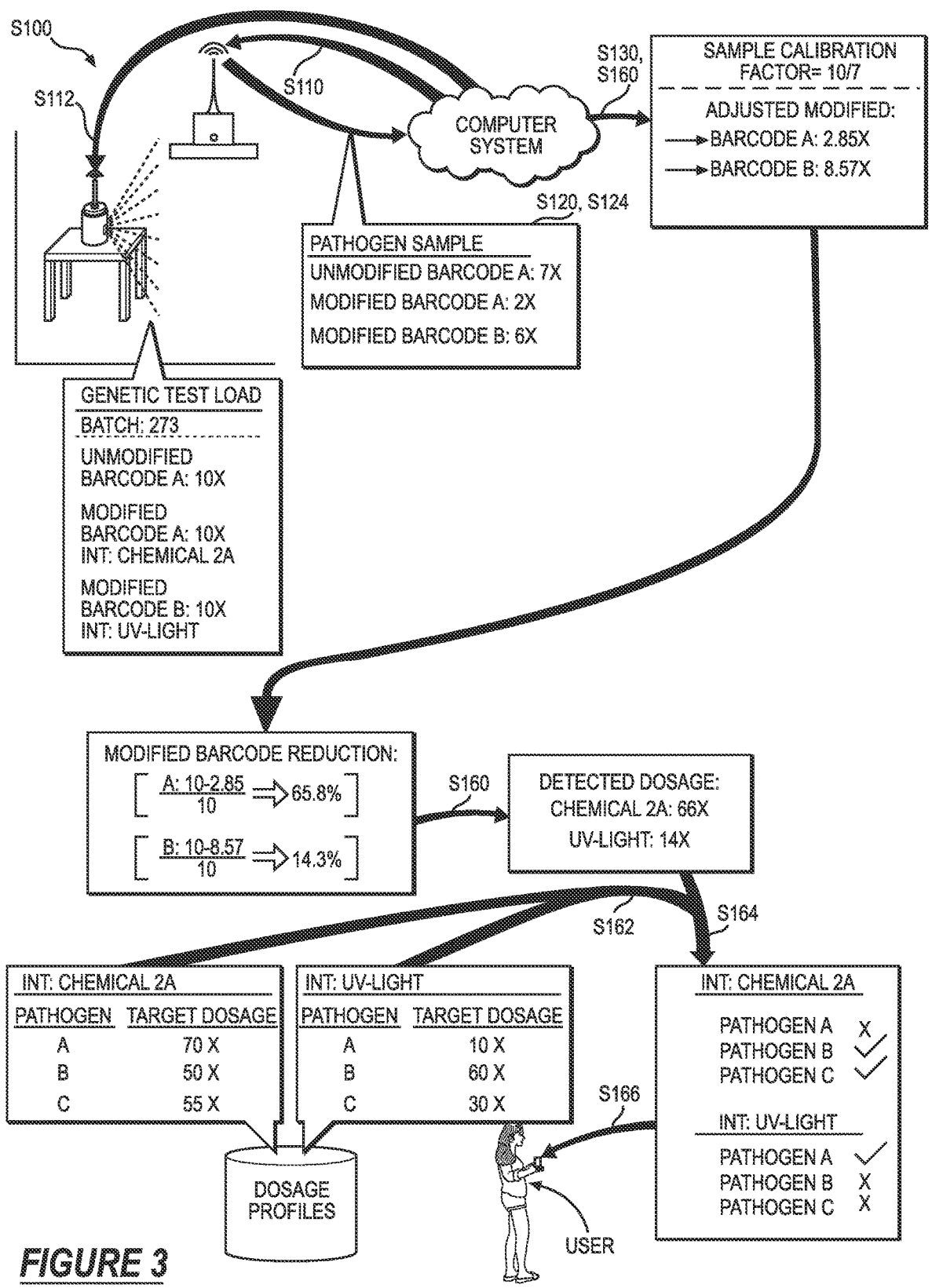
FIG. 3 is a flowchart representation of the method.
Figure 4A:
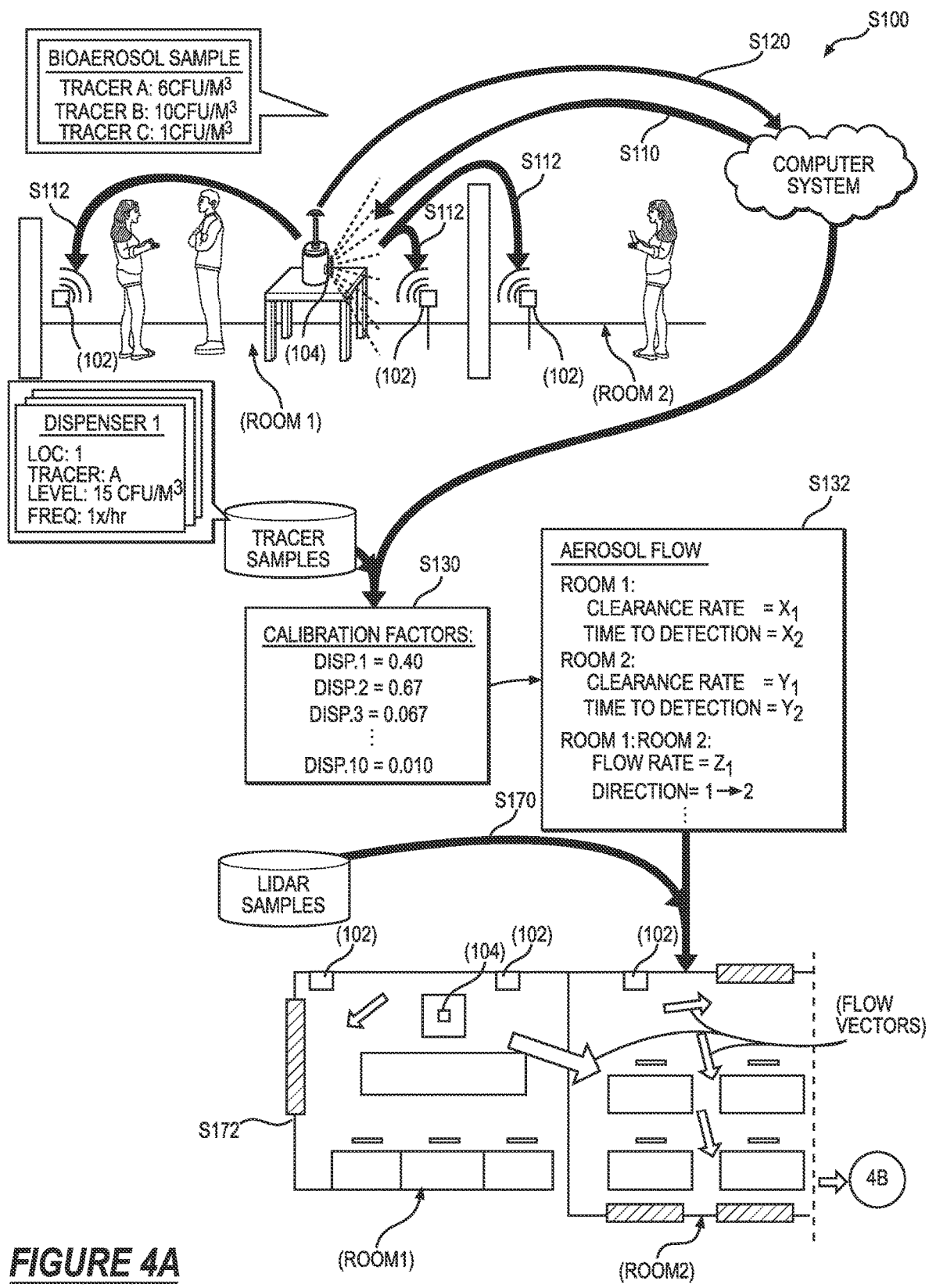
FIGS. 4A and 4B are flowchart representations of the method.
Figure 4B:
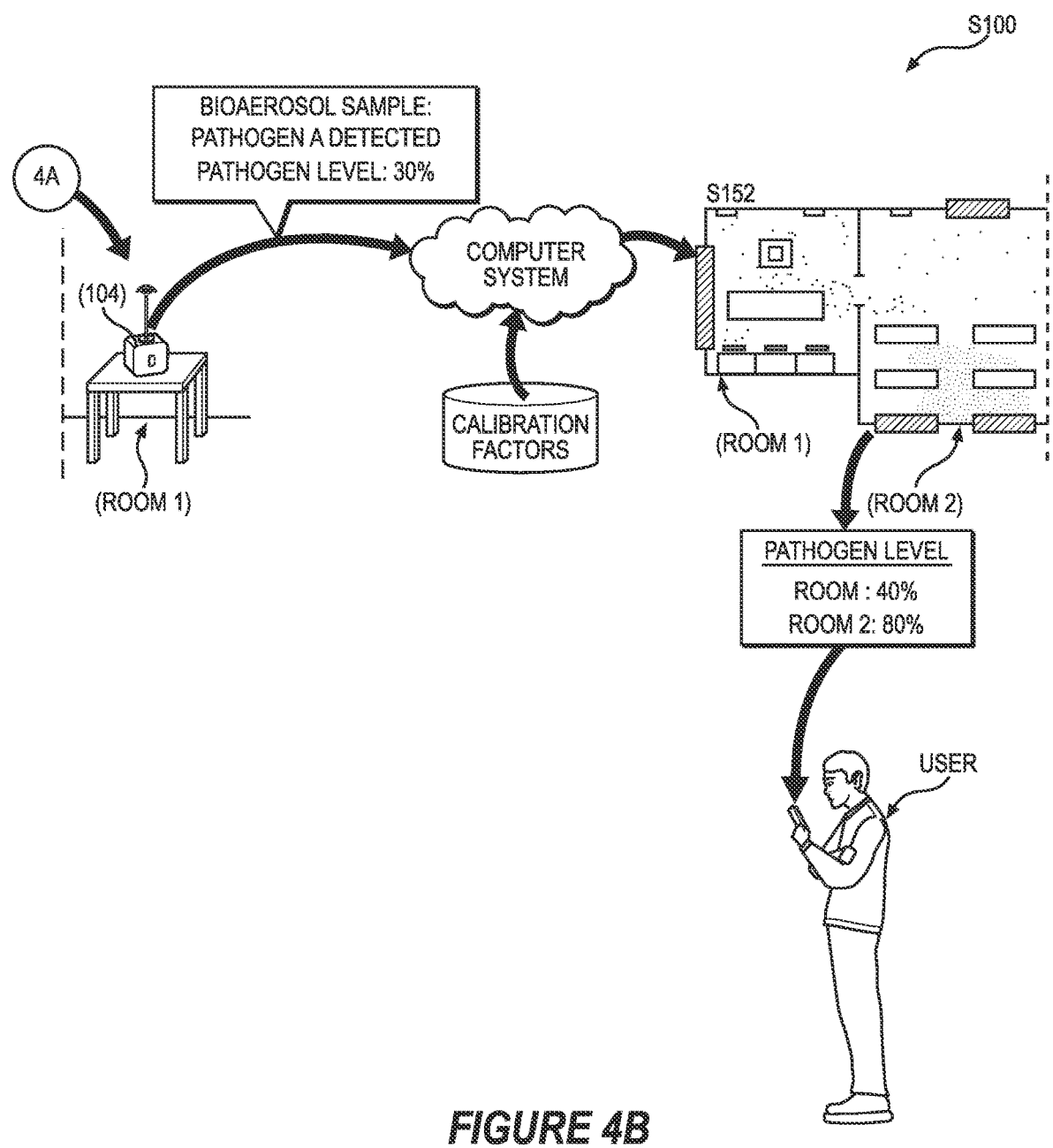

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

As shown in FIGS. 1-3, 4A, and 4B, a method S100 includes, during a calibration period for an environment: triggering collection of an initial bioaerosol sample over an initial sampling period of a fixed duration by an air sampler located in the environment in Block S110; during the first sampling period, triggering dispensation of a first tracer test load by a dispenser located in the environment, the first tracer test load including a set of barcodes in solution in Block S112; accessing a first detected barcode level of a first barcode, in the set of barcodes, detected in the initial bioaerosol sample in Block S120; accessing a first true barcode level of the first barcode present in the first tracer test load in Block S122; and deriving a first calibration factor, in a set of calibration factors, for the first barcode in the environment based on a difference between the first detected barcode level and the first true barcode level in Block S130. The method S100 further includes, during a live period succeeding the calibration period: triggering collection of a first bioaerosol sample over a first sampling period of the fixed duration by the air sampler in Block S140; accessing a first detected pathogen level of a first pathogen, in a set of pathogens, present in the first bioaerosol sample in Block S150; and predicting a first pathogen level of the first pathogen in the first bioaerosol sample based on the first detected pathogen level and the first calibration factor in Block S152.

One variation of the method S100 further includes, in response to the first pathogen level exceeding a threshold pathogen level: selecting a first mitigation technique, in a set of mitigation techniques, configured to reduce the first pathogen level of the first pathogen in Block S180; generating a prompt to execute the first mitigation technique in the environment; and transmitting the prompt to a user associated with the environment in Block S182.

One variation of the method S100 includes, during a calibration period for an environment: triggering collection of an initial bioaerosol sample over an initial sampling period of a fixed duration by an air sampler located in the environment in Block S110; during the first sampling period, triggering dispensation of a first tracer test load by a dispenser located in the environment, the first tracer test load including fluorescent material in solution in Block S112; accessing a first detected fluorescence level of fluorescent material detected in air collected by the air sampler in Block S120; accessing a first true fluorescence level of fluorescent material present in the first tracer test load in Block S122; and deriving a fluorescence calibration factor for fluorescent material in the environment based on a difference between the first detected fluorescence level and the first true fluorescence level in Block S130. In this variation, the method S100 further includes, during a live period succeeding the calibration period: triggering collection of a first bioaerosol sample over a first sampling period of the fixed duration by the air sampler in Block S140; accessing a first detected pathogen level of a first pathogen, in a set of pathogens, present in the first bioaerosol sample in Block S150; and predicting a first pathogen level of the first pathogen in the first bioaerosol sample based on the first detected pathogen level and the first calibration factor in Block S152.

One variation of the method S100 includes, during a calibration period for an environment: triggering collection of a first bioaerosol sample, over a first sampling period, by an air sampler installed in the environment in Block S110; at a first time during the first sampling period, triggering dispensation of a first tracer test sample by a first dispenser installed in a first location in the environment, the first tracer test sample including a first true tracer level of tracer molecules of a first type in solution in Block S120; and at approximately (e.g., within 1 second, within 30 seconds, within 1 minute) the first time, triggering dispensation of a second tracer test sample by a second dispenser installed in a second location in the environment, the second tracer test sample including a second true tracer level of tracer molecules of a second type in solution in Block S120; accessing a first detected level of tracer molecules of the first type present in the bioaerosol sample in Block S122; accessing a second detected level of tracer molecules of the second type present in the bioaerosol sample in Block S122; deriving a first calibration factor, in a set of calibration factors, for tracer molecules dispensed from the first dispenser at the first location based on a first difference between the first detected tracer level and the first true tracer level in Block S130; deriving a second calibration factor, in the set of calibration factors, for tracer molecules dispensed from the second dispenser at the second location based on a second difference between the second detected tracer level and the second true tracer level in Block S130; and interpreting a set of aerosol flow patterns in the environment based on the set of calibration factors in Block S132. In this variation, this method S100 can further include, during a live period succeeding the calibration period: triggering collection of a second bioaerosol sample, over a second sampling period, by the air sampler in Block S140; accessing a first pathogen level of a first pathogen, in a set of pathogens, present in the second bioaerosol sample in Block S150; and predicting a pathogen level gradient of the first pathogen in the environment, during the second sampling period, based on the first pathogen level and the set of aerosol flow patterns in Block S152.

One variation of the method S100 includes: triggering collection of a first bioaerosol sample by an air sampler located in the environment over a first sampling period of a fixed duration in Block Silo; and during the first sampling period, triggering dispensation of a first tracer test load by a dispenser in the environment, the first tracer test load including a first amount of an unmodified barcode and a second amount of a modified barcode corresponding to the unmodified barcode and linked to a first intervention type in Block S112; accessing a first detected amount of the unmodified barcode present in the first bioaerosol sample collected by the air sampler during the first sampling period in Block S120; deriving a calibration factor, in a set of calibration factors, based on the first amount and the first detected amount of the unmodified barcode in Block S130; accessing a second detected amount of the modified barcode detected in the first bioaerosol sample in Block S124; predicting an adjusted detected amount of the modified barcode present in the environment, during the first sampling period, based on the second detected amount and the calibration factor in Block S160; and characterizing a detected dosage of the first intervention type in the environment during the first sampling period based on a difference between the adjusted detected amount and the second amount of the modified barcode dispensed in the first tracer test load in Block S162.

In one variation, the method S100 further includes accessing a dosage profile corresponding to the first intervention type in Block S162. In this variation, the method S100 further includes, for each pathogen in a set of pathogens defined for the environment: accessing a target dosage, in a set of target dosages, of the first intervention type configured to mitigate pressures (e.g., presence and/or magnitude) of the pathogen; and characterizing a dosage difference, in a set of dosage differences, between the detected dosage and the target dosage for the pathogen in Block S164. In this variation, the method S100 can further include: generating a notification including the set of dosage differences corresponding to the set of pathogens; and transmitting the notification to a user associated with the environment in Block S166.

One variation of the method S100 includes, during a calibration period for an environment: triggering collection of a first bioaerosol sample over a first sampling period of a fixed duration by an air sampler installed in the environment in Block Silo; during the first sampling period, triggering dispensation of a tracer test load by a first dispenser, in a set of dispensers, installed in the environment, the tracer test load including tracer molecules in solution in Block S112; accessing a detected amount of tracer molecules present in the first bioaerosol sample in Block S120; accessing a true amount of tracer molecules present in the tracer test load in Block S122; deriving a calibration factor, in a set of calibration factors, for the environment based on a difference between the detected amount of tracer molecules and the true amount of tracer molecules in Block S130; deriving a set of aerosol flow metrics, representing movement of aerosols in the environment, based on the set of calibration factors in Block S132; accessing a set of images of the environment recorded by a set of optical sensors deployed in the environment during the calibration period in Block Silo; and deriving an aerosol flow map depicting movement of bioaerosols within the environment based on the set of images and the set of air flow metrics in Block S172.

In one variation, the method S100 further includes, during a live period succeeding the calibration period: triggering collection of a second bioaerosol sample over a second sampling period of the fixed duration by the air sampler in Block S140; accessing a detected pathogen level of a first pathogen, in a set of pathogens, present in the second bioaerosol sample in Block S150; predicting a first pathogen level, in a set of pathogen levels, of the first pathogen in a first location, in a set of locations, in the environment during the second sampling period based on the detected pathogen level and the aerosol flow map in Block S152; and predicting a second pathogen level, in the set of pathogen levels, of the first pathogen in a second location, in the set of locations, in the environment during the second sampling period based on the detected pathogen level and the aerosol flow map in Block S152.

One variation of the method S100 includes, during a calibration period for a space: triggering collection of a first bioaerosol sample by an air sampler 104 located in the space during a first sampling window of a target duration in Block Silo; and triggering dispensation of a first tracer test load containing a first barcode by a dispenser 102 located in the space during the first sampling window in Block S112. The method S100 further includes: accessing a detected barcode level of a first barcode detected in the first bioaerosol sample collected by the air sampler 104 during the first sampling window in Block S120; accessing a true barcode level of the first barcode contained in the first tracer test load dispensed by the dispenser 102 during the first sampling window in Block S122; deriving a first calibration factor for the space based on a difference between the detected barcode level and the true barcode level in Block S130; and storing the first calibration factor in a calibration profile for the space in Block S132. The method S100 further includes, during a live period succeeding the calibration period, triggering collection of a second bioaerosol sample by the air sampler 104 during a second sampling window of the target duration in Block S140. The method S100 also includes: accessing a detected pathogen level of a first pathogen, in a set of pathogens, detected in the second bioaerosol sample collected by the air sampler 104 during the second sampling window in Block S150; and calculating a predicted pathogen level of the first pathogen in the second bioaerosol sample based on the detected pathogen level and the first calibration factor in Block S170.

One variation of the method S100 further includes, in response to the predicted pathogen level exceeding a threshold pathogen level, transmitting a prompt to a user, associated with the space, to manage the first pathogen within the space in Block S180.

2. Pathogen Detection System

As shown in FIGS. 1-3, 4A-4B, 5A-5C, 6, and 7, a pathogen detection system 100 includes a molecular tracer dispenser 102 (hereinafter a "dispenser 102") and an air sampler 104.

The dispenser 102 is installed in an enclosed environment and includes: a dispenser cartridge 130 containing DNA barcodes and fluorescent material; a dispenser communication module 120 configured to receive commands for operation of the dispenser 102; and an actuator 116 configured to release a solution dose from the dispenser cartridge 130 based on a command received by the dispenser communication module 120.

One variation of the dispenser 102 includes: a dispenser cartridge 130 containing DNA barcodes; a dispenser communication module 120 configured to receive commands for operation of the dispenser 102; and an actuator 116 configured to release a solution dose from the dispenser cartridge 130 based on a command received by the dispenser communication module 120.

One variation of the dispenser 102 includes: a dispenser cartridge 130 containing fluorescent material; a dispenser communication module 120 configured to receive commands for operation of the dispenser 102; and an actuator 116 configured to release a solution dose from the dispenser cartridge 130 based on a command received by the dispenser communication module 120.

The air sampler 104 is installed in the enclosed environment and includes: a sampler housing 150 defining an air inlet and an air outlet; a tunnel 152 arranged within the sampler housing 150 and extending between the air inlet and the air outlet; and a sampler cartridge 160 configured to collect bioaerosols in air flowing through the tunnel 152.

The pathogen detection system can further include a controller configured to: coordinate operation of the dispenser 102; and coordinate operation of the air sampler 104.

One variation of the pathogen detection system 100 includes a molecular tracer dispenser 102 (or "dispenser 102") including: a housing 110 defining a fluid outlet and a cartridge inlet; a cartridge receptacle 112 located within the housing 110 proximal the cartridge inlet; a loading vessel 117 located within the housing 110; a fluid reservoir 140 fluidly coupled to the loading vessel 117 and configured to store volumes of an aqueous solution; a fluid doser configured to dispense a volume of the aqueous solution into the loading vessel 117; a sprayer 118 (e.g., an aerosolizer) arranged proximal the outlet, fluidly coupled to the loading vessel 117, and configured to dispense droplets of a tracer test load contained in the loading vessel 117 into an external environment surrounding the housing 110; a power supply; and a dispenser communication module 120 configured to receive commands for operation of the dispenser 102. In this variation, the pathogen detection system 100 further includes a dispenser cartridge 130 including: a set of tracer reservoirs 132, each tracer reservoir 132, in the set of tracer reservoirs 132, preloaded with a concentrated barcode sample, in a set of concentrated tracer samples (e.g., barcode samples and/or fluorescent material samples), configured for release into the loading vessel 117 to generate the tracer test load; and a connector configured to insert into the cartridge inlet and transiently engage with the cartridge receptacle 112, to locate the set of tracer reservoirs 132 within the dispenser 102.

In one variation, the dispenser 102 can further include a controller configured to selectively actuate the sprayer 118 to dispense droplets of the tracer test load.

In one variation, the dispenser 102 includes a fluid accumulator, located proximal the set of tracer reservoirs 132 within the housing 110, and configured to direct fluid released from the set of tracer reservoirs 132 into the loading vessel 117.

In another variation, the molecular tracer dispenser 102 further includes a cleaning module configured to sanitize surfaces within the molecular tracer dispenser 102 in preparation for a dispense cycle.

One variation of the pathogen detection system 100 includes: a molecular tracer dispenser 102 configured to release tracer test loads into a surrounding space; and an air sampler 104 configured to draw air from the surrounding space and through an inlet of the air sampler 104 to collect a bioaerosol sample.

One variation of the pathogen detection system 100 includes: a set of molecular tracer dispensers 102 distributed throughout a facility, each molecular tracer dispenser 102, in the set of molecular tracer dispensers 102, configured to release tracer test loads into a surrounding space within the facility; and a set of air samplers 104 distributed throughout the facility, each air sampler 104, in the set of air samplers 104, configured to draw air from the surrounding space and through an inlet of the air sampler 104 to collect a bioaerosol sample.

3. Applications

Generally, the pathogen detection system 100 includes a molecular tracer dispenser 102 (hereinafter a "dispenser 102") configured to: dispense a known (or "calibrated") amount of a molecular tracer molecule (hereinafter a "barcode")— contained in a tracer test load—into a space (or "environment") (e.g., an indoor environment); control characteristics—such as barcode identity (e.g., defined by a DNA sequence of the barcode), barcode size (e.g., molecular size), barcode concentration (e.g., in the tracer test load), timing of dispensation—of tracer test loads dispensed into the space; and track characteristics of genetic tests loads sequentially and selectively released into the space over time. The system also includes an air sampler 104 configured to: collect a bioaerosol sample during or after release of barcodes into the space; and detect presence and amount (or magnitude, signal strength) of bioaerosols—including tracer molecules (e.g., barcodes and/or fluorescent material) and/or pathogens present in air collected by the air sampler 104—in the bioaerosol sample.

Generally, Blocks of the method 100 can be executed by a computer system (e.g., a remote computer system, a local server) in conjunction with the pathogen detection system 100 (hereinafter the "system") to: dispense a known (or "calibrated") amount of a molecular tracer molecule (hereinafter a "barcode") into a space; collect a bioaerosol sample during or after release of barcodes into the space; detect presence and amount (or magnitude, signal strength) of the barcode in the bioaerosol sample; and derive a calibration factor representative of detectability of these barcodes—and therefore airborne particles more generally (e.g., airborne pathogens) within the space—based on a difference between the known amount of dispensed barcode and the amount of the barcode detected in the bioaerosol sample.

The system can also execute Blocks of the method to identify instances and/or triggers for reduced or limited detectability of such barcodes in bioaerosol samples— and therefore airborne particles more generally over time— based on differences between amounts of the barcode dispensed by the dispenser 102 and amounts of the barcode detected in bioaerosol samples captured by the air sampler 104 over time throughout the calibration period, such as due to placement of the air sampler 104 within the space or resulting from environmental changes within the space over time. Accordingly, the system can: track or access data streams for local conditions within the space (e.g., air temperature, humidity, time of day, indoor air velocity, human occupancy) during the calibration period; and define a calibration factor (or a "calibration model") for the space as a function of such local conditions present in the space during the calibration period.

Later, during a live (or "operating") period, the air sampler 104 can collect a bioaerosol sample of the space. The system can thus: detect presence and amount (or magnitude, signal strength) of a pathogen in this bioaerosol sample; and then implement the calibration factor to interpret (or correct, normalize) the detected amount of the pathogen present in the bioaerosol sample based on the calibration factor (and current local conditions in the space). More specifically, the system can implement the calibration factor to estimate a true magnitude of the pathogen present in the space based on an uncorrected pathogen load detected in a bioaerosol sample captured by the air sampler 104. The system can then selectively generate and distribute prompts related to improving detectability of pathogens and/or mitigating pathogen detected in the space based on this true pathogen load.

In one implementation, the air sampler 104 is deployed in a particular space (e.g., a classroom, an office, a shop, an airport terminal) and configured to ingest air present in this particular space and to capture bioaerosol samples (e.g., air samples containing captured airborne pathogens) from air in this particular space. In this implementation, the molecular tracer dispenser 102 is deployed in the particular space (e.g., permanently or exclusively during the calibration period) and is configured to release airborne tracer test loads—including known concentrations of tracer molecules (e.g., barcodes, fluorescent material)—into air in this particular space. During a calibration period for this particular space, the system can trigger collection of a bioaerosol sample at the air sampler 104 and concurrently trigger release of a tracer test load from the molecular tracer dispenser 102. The system (or an external lab or sensor) can then analyze (e.g., via genetic sequencing) this bioaerosol sample to calculate a detected amount (or concentration, level) of these barcodes, which represents a proportion of the tracer test load detectable (or "visible") to the air sampler 104 within a sampling window. The remainder of the tracer test load not captured by the air sampler 104 can therefore remain in the space. Similarly, during a live period, the air sampler 104 can capture a portion of a total amount of a pathogen present in the space. The remainder of this pathogen not captured by the air sampler 104 can therefore remain in the space, and the ratio of detected pathogen to pathogen remaining in the space (or total pathogen load present in the space prior to bioaerosol sample capture) during the live period can be similar to the ratio of detected tracer molecule to tracer molecule remaining in the space (or total tracer molecule load present in the space prior to bioaerosol sample capture) during the calibration period.

The system can therefore derive a calibration factor for the space (and or for particular set of environmental conditions, tracer molecule size, etc.) based on the known concentration of these barcodes released by the dispenser 102 and the detected concentration of these barcodes in the bioaerosol sample captured during the calibration period. The system can then leverage this calibration factor to predict actual concentrations of pathogens in this space based on concentrations of these pathogens detected in subsequent bioaerosol samples collected by this air sampler 104 in this space.

Additionally, the system can leverage similarities between tracer molecules and pathogens (e.g., bacteria, viruses) to mimic flow or dispersion of these pathogens within the space. For example, the molecular tracer dispenser 102 can be configured to release tracer molecules exhibiting a range of sizes, such that pathogens of different sizes (e.g., within the range of sizes) can be linked to a particular tracer molecule most representative of this particular tracer molecule. Therefore, the system can derive a set of calibration factors during this calibration period, each calibration factor corresponding to a particular tracer molecule. This system can then leverage this set of calibration factors to predict pathogen levels of different types of pathogens in the space.

Further, the system can leverage detection of these tracer molecules to identify regions within a space exhibiting relatively low detectability and regions exhibiting relatively high detectability. For example, the system can include multiple dispensers 102 deployed in different regions of a single space, each dispenser 102 configured to release tracer test loads of different tracer molecule types. The system can then identify a detected tracer concentration for each tracer molecule type, and, based on a known concentration of each tracer molecule output by a corresponding dispenser 102, identify a proportion of tracer molecules detectable for each tracer test load. Then, based on these proportions and the locations of each of the dispensers 102 in the network, the system can: identify which regions of the space exhibit high detectability and which regions exhibit low detectability; and derive calibration factors representative of detectability, flow, dispersion, and/or other behaviors (e.g., bioaerosol clearance rate, bioaerosol exposure reduction rate) of these barcodes and therefore airborne particles more generally.

The system can continue to trigger release of tracer test loads by the dispenser 102 after the calibration period to monitor changes in detectability of tracer molecules in the space. In particular, based on a calibration factor derived during the calibration period, the system can estimate an expected concentration in any bioaerosol sample collected by the air sampler 104. If, however, the detected tracer molecule concentration is less than this expected concentration, the system can prompt a user associated with the space to investigate the space for possible causes of interference, such as due to changes in airflow, barriers, occupancy, dilution, disinfection, etc. Additionally and/or alternatively, the system can identify a cause of this interference and prompt the user to implement a mitigation technique—matched to this cause of interference—to restore detection of tracers and/or pathogens in this space.

3.1 Dispenser: Deployment, Sample Preparation, and Controlled Release

The dispenser 102 can be installed within a particular space within a facility—such as fixed to a wall, mounted on a surface (e.g., of a table), or coupled to an electrical outlet—to release tracer test loads of particular barcodes in this particular space. In particular, the system can include a network of dispensers 102 distributed throughout the facility. Each dispenser 102, in the network of dispensers 102, can include a communication module 120 configured to enable communication (e.g., via Wi-Fi) between the dispenser 102 and the computer system (e.g., a remote computer system, a local server), each other dispenser 102 in the network of dispensers 102, and/or a set of air samplers 104 installed in the particular space.

In particular, the dispenser 102 is configured to receive a dispenser cartridge 130 (hereinafter "cartridge 130")—loaded with a set of barcode samples (e.g., highly-concentrated barcode samples)—to dispense particular barcodes, contained in the set of barcode samples in the cartridge 130, into the space. Over time, this cartridge 130 can be replaced to replenish a supply of barcode samples available for dispensation by the dispenser 102 and/or to supply the dispenser 102 with different types of barcode samples. Once deployed (e.g., permanently or temporarily installed) to a particular space, the dispenser 102 can release tracer test loads—including controlled amounts (e.g., concentrations), sizes, and identities of barcodes—during dispense cycles of controlled durations and executed at controlled frequencies, such as once per minute, once per hour, once per day, once per week, or continuously. Then, approximately concurrent initiation of a dispense cycle, the system can trigger the air sampler 104 to initiate a sampling period. During this sampling period, the air sampler 104 can: ingest air from the space (e.g., for a target duration of the sampling period); draw this air over an internal collection subsystem to collect a bioaerosol sample from the space; and process this bioaerosol sample to detect presence and/or magnitude of various genetic material (or pathogens and/or barcodes specifically) in the space.

In one implementation, the system includes a network of dispensers 102 (e.g., multiple dispensers 102) distributed throughout different regions of a space or facility. In this implementation, the network of dispensers 102 can be configured to release tracer test loads—including known amounts of barcodes of known concentrations, barcodes types, and/or identities—at fixed frequencies (e.g., once-per-minute, once-per-hour, once-per-day, once-per-week) in concert with collection of bioaerosol samples by one or more air samplers 104 installed in the space or facility. In particular, the system can trigger each dispenser 102, in the network of dispensers 102, to dispense a tracer test load, in a set of tracer test loads, at controlled and/or scheduled release times, each tracer test load, in the set of tracer test loads, including known (or "standardized") concentrations of a set of standardized barcodes, such that each tracer test load is released at approximately the same time and includes approximately identical concentrations of an identical set of standardized barcodes. Therefore, by coordinating timing, concentration, and identity of barcodes released into the space and/or facility across the network of dispensers 102, the system can derive insights related to detectability, flow, and/or dispersion of bioaerosols in different regions of the space and/or facility.

4. Air Sampler

The pathogen detection system 100 includes an air sampler 104 configured to draw air from an external environment (e.g., surrounding the air sampler 104) into the air sampler 104 to extract bioaerosol samples from the air. Generally, the air sampler 104 is configured to transiently or semi-permanently install in a particular environment (e.g., an enclosed space within a building), such as such as fixed to a wall, mounted on a stand, or standing on a floor of a particular room. Alternatively, the air sampler 104 can be coupled with a mobile apparatus (e.g., a manual or autonomously cart, an autonomous aerial vehicle) configured to transport the air sampler 104 about a space or facility. The air sampler 104 can then directly sample air from this environment and locally (and/or remotely) implement pathogen detection. For example, the air sampler 104 can be mounted (e.g., transiently, permanently) to a mobile robot (e.g., a UGV) configured to autonomously navigate between different rooms within an office building to monitor pathogen levels across each of these rooms.

Further, the system can include multiple air samplers 104 installed throughout a particular facility (e.g., one per floor in an office building). For example, the system can include a docking station (e.g., a charging docking station) configured to house a set of air samplers 104, such that each air sampler 104 can be deployed from the docking station to a particular space (e.g., an office, a classroom, a store, a bathroom) within a larger facility (e.g., an office building, a school, a mall, an airport).

Once deployed (e.g., permanently or temporarily installed) in a particular space, the air sampler 104 can ingest air from the space over time and draw this air over an internal collection subsystem to collect bioaerosol samples from the space, such as once per day, once per hour, once per minute, or continuously. An internal genetic material load detector, selective pathogen detector, or DNA sequencer within the air sampler 104 can then process these bioaerosol samples to detect presence and/or magnitude (e.g., pathogen level) of various genetic material (or viral and/or bacterial pathogens specifically) in the space, and the air sampler 104 can then assemble detected presence and/or magnitudes of genetic material thus detected in the space over time into pathogen data representing presence and/or magnitude of genetic material in air within the space (e.g., at a particular time and/or over time). Alternatively, bioaerosol samples collected by the air sampler 104 can be intermittently returned to a lab for processing and diagnostics, such as by: removing a first sampler cartridge 160—including a first collector plate containing a first bioaerosol sample—from the air sampler 104; installing a second sampler cartridge 160 into the air sampler 104 in preparation for a next air capture period; and returning the first sampler cartridge 160 to the lab for remote processing.

In one implementation—as described in U.S. patent application Ser. No. 17/709,213, filed on 30 Mar. 2022, which is incorporated in its entirety by this reference—the air sampler 104 can be configured to include an air-capture module configured to draw air from the environment through the inlet of the body via electrostatic forces. This "electrostatic air sampler 104" can include: a charging element; a sampling medium in the form of a collector plate; and a power supply air-capture module configured to apply a voltage across the collector plate. For example, the electrostatic air sampler 104 can include: an inlet configured to transfer a bioaerosol sample from a surrounding space into the electrostatic air sampler 104; a collector plate configured to receive the bioaerosol sample and collect pathogens present in the bioaerosol sample; and a corona wire configured to cooperate with the collector plate to draw the bioaerosol sample through the inlet via electrostatic forces. In particular, in this example, the air sampler 104 can be configured to supply a voltage between the corona wire and the collector plate to enable ionization of particles present in the bioaerosol sample, thereby accelerating these particles through the inlet and onto the collector plate.

Figure 6:
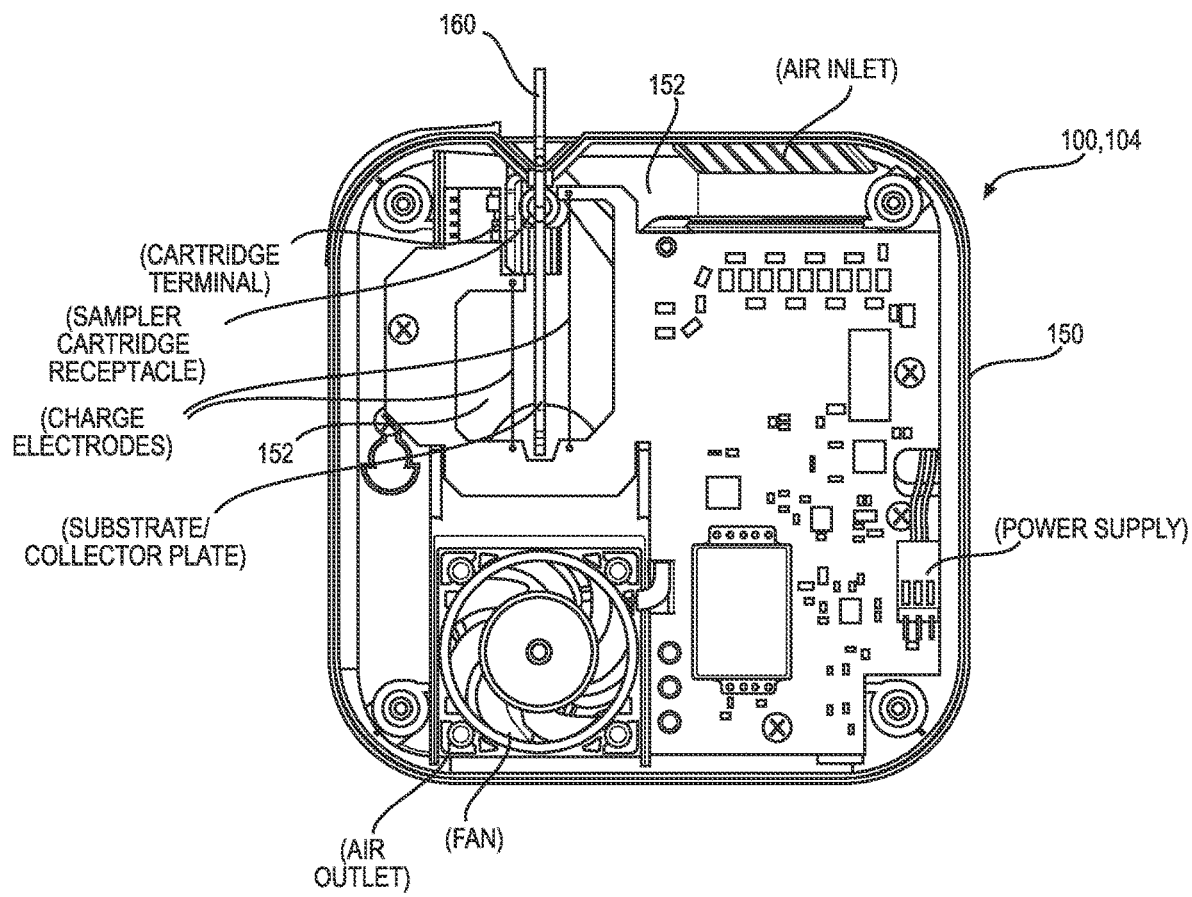
FIG. 6 is a schematic representation of the system.
Figure 7:
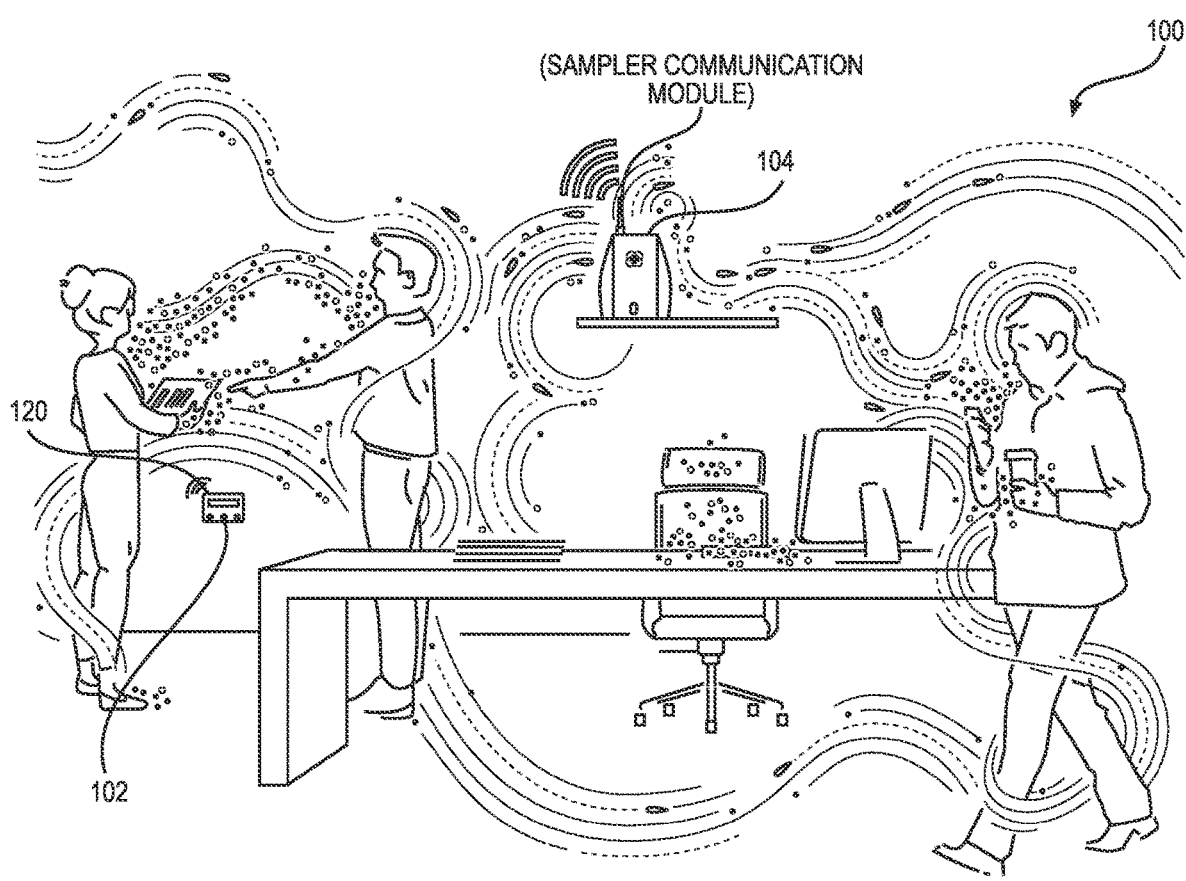
FIG. 7 is a schematic representation of the system.

In one example of the preceding implementation, as shown in FIG. 6, the air sampler 104 can include: a sampler housing 150 defining an inlet and an outlet; a tunnel 152 extending between the inlet and the outlet within the sampler housing 150; a charge electrode arranged within the tunnel 152 proximal the inlet; a sampler cartridge receptacle arranged proximal the fluid outlet within the sampler housing 150 and including a cartridge terminal; and a power supply configured to drive a voltage between the charge electrode and the cartridge terminal. In this example, the pathogen detection system can further include a sampler cartridge 160 including: a substrate (e.g., a printed circuit board); a collector plate arranged on the substrate and configured to collect charged bioaerosols moving through the tunnel 152; and a connector configured to transiently engage the sampler cartridge receptacle to locate the substrate and the collector plate within the tunnel 152 and electrically couple the collector plate to the cartridge terminal.

Alternatively, in another implementation, the air sampler 104 can be configured to include an air-capture module including a pump coupled to the inlet of the air sampler 104 and configured to draw air from the inlet and onto a sampling medium within a body of the air sampler 104 at a target rate (e.g., once cubic foot per second). This "pump-based air sampler 104" can include a sampling medium in the form of a filter cartridge (e.g., a PTFE filter cassette). For example, the pump-based air sampler 104 can actuate the pump to draw air through the inlet and through the filter cartridge such that particles in the air collect on a filter within the filter cartridge. The pump-based air sampler 104 can thus continue to actuate the pump to dry and thus concentrate these particles on the filter over a sampling period, such as of a predefined duration (e.g., 30 seconds).

In each of these implementations, the air sampler 104 can further include: a controller including a set of electronics and configured to selectively actuate components of the air sampler 104; and a communication module 120 configured to transmit data between the air sampler 104, a set of dispensers 102, other air samplers 104, a set of external devices (e.g., a mobile device, a local computing device), and/or a computer system (e.g., a local server, a remote computer system).

4.1 Detection

The system can be configured to detect presence and/or magnitude of a set of pathogens within bioaerosol samples collected in the space. Further, the system can detect presence and/or magnitude of tracer molecules (e.g., a set of barcodes and/or fluorescent material)—present in tracer test loads released by the dispenser 102—captured in bioaerosol samples collected by the air sampler 104.

In one implementation, the air sampler 104 can be configured to process these bioaerosol samples for diagnostics and/or genetic sequencing directly within the air sampler 104. For example, in this implementation, the air sampler 104 can include: a set of sensors in the sampler cartridge 160 (e.g., coupled to and/or arranged proximal the collector plate) configured to detect tracer molecules (e.g., barcodes and/or fluorescent material) and/or pathogens in bioaerosol samples (e.g., fluid or dry bioaerosol samples) collected by the air sampler 104; and a controller configured to read a set of signals from the set of sensors (e.g., via a databus) and interpret levels of tracer molecules and biological pathogens in air flowing through the tunnel 152 based on the set of signals.

In particular, in this implementation, the air sampler 104 can include: a detection module configured to receive the bioaerosol sample for genetic testing; and a handoff configured to transfer a collected bioaerosol sample from the sampling medium to the detection module for pathogen detection (e.g., via genetic testing). Further, the detection module can include a processing stage configured to process the bioaerosol sample in preparation for diagnostics and/or genetic sequencing. For example, at an expiration of a sampling window, the air sampler 104 can transfer a bioaerosol sample from the sampling medium to the processing stage of the detection module via the handoff. Then, at the processing stage, the air sampler 104 can: lyse DNA and/or RNA fragments in the bioaerosol sample; concentrate these DNA and/or RNA fragments within the bioaerosol sample; and compile these fragments from the bioaerosol sample into a genetic library (e.g., a DNA and/or RNA library) for genetic sequencing. The bioaerosol sample—now prepared into the genetic library—can then be passed through a genetic sequencer (e.g., a nanopore genetic sequencer, a LAMP reactor) configured to identify a set of pathogens present in the bioaerosol sample.

Alternatively, in another implementation, the air sampler 104 can be configured to store this bioaerosol sample for further processing at a remote location (e.g., in a laboratory). In this variation, the air sampler 104 can be configured to collect the bioaerosol sample at the sampling medium and store the bioaerosol sample (e.g., in a storage module) within the air sampler 104 for later collection. For example, the air sampler 104 can be configured to: collect a bioaerosol sample each day for a week (e.g., to collect 7 bioaerosol samples, one for each day of the week); and store each bioaerosol sample on a different sampler cartridge within the air sampler 104. In particular, in this example, the air sampler 104 can be configured to include a carousel housing a set of sampler cartridges, such that the air sampler 104 can actuate the carousel each day to rotate a fresh (i.e., clean, empty) sampler cartridge into a sampling position, each sampler cartridge linked to a corresponding day of the week. A user (e.g., associated with the space) can then: collect the set of sampler cartridges from the carousel at an end of the week for further testing offsite; and refill the carousel with a new set of sampler cartridges for the next week.

5. Molecular Tracer Dispenser

The pathogen detection system 100 includes a molecular tracer dispenser 102 (hereinafter a "dispenser 102") configured to transiently or semi-permanently install in a particular environment and to release tracer test loads (e.g., droplets of DNA barcodes and/or fluorescent material in solution) into the environment (e.g., surrounding the dispenser 102). In particular, the system can include a dispenser 102 configured to intermittently dispense tracer test loads containing known quantities of molecular tracer molecules.

In one implementation, the dispenser 102 can be configured to output tracer test loads containing DNA barcodes (or "barcodes") (e.g., short sections of DNA from a particular gene or set of genes). In this implementation, the dispenser 102 can be configured to output tracer test loads containing a set of barcodes (e.g., exhibiting negligible or no impact on human health). The system can leverage these DNA barcodes (or "barcodes") as markers in bioaerosol samples collected by the air sampler 104. In particular, the dispenser 102 can be configured to output tracer test loads containing tracer molecules configured to mimic flow, distribution, and/or dissipation of pathogens (e.g., output in human saliva) in the space. For example, the dispenser 102 can release a tracer test load including: a first barcode exhibiting sizes (e.g., relatively small sizes) within a first size range matched to pathogens exhibiting sizes within the first size range; and a second barcode exhibiting sizes (e.g., relatively large sizes) within a second size range matched to pathogens exhibiting sizes within the second size range; and a third barcode exhibiting sizes (e.g., relatively moderate sizes) within a third size range between the first and second size range. Therefore, the system can leverage detection of these barcodes—which can exhibit different flow or distribution patterns within a space based on their sizes—to better predict flow or distribution of viruses of different sizes within the space.

The dispenser 102 can be configured to output a tracer test load of a known volume and including a known concentration of barcodes, such that the system can compare a detected barcode level (e.g., amount, quantity, concentration) to a real barcode level (e.g., based on the known volume and the known concentration) in the tracer test load released by the dispenser 102. Further, the dispenser 102 can be configured to intermittently release tracer test loads into the space, such as at a target frequency and/or aligned with collection of bioaerosol samples by the air sampler 104.

In particular, the air sampler 104 (or another device configured for genetic sequencing) implements a DNA sequencer to detect presence and load of tracer molecules and/or microbes (e.g., pathogens) in a bioaerosol sample captured by the air sampler 104 during a sampling window. The dispenser 102 dispenses barcodes with unique molecular (e.g., genetic) identifiers that can be detected and identified by the same DNA sequencer. Therefore, the calibration factor derived by the system from known amounts of dispensed barcode and detected amounts of barcode in a bioaerosol sample captured during the calibration routine is calibrated to both the space and the DNA sequencer, such as to both environmental conditions (e.g., air currents, air cycling, barriers, traffic) in this space and the sensitivity of the DNA sequencer to genetic material of different types and sizes.

In one implementation, the air sampler 104 and the dispenser 102 can be configured to wirelessly communicate with one another, such that the dispenser 102 can automatically trigger the air sampler 104 to collect a bioaerosol sample in preparation for or responsive to dispensation of a tracer test load and/or the air sampler 104 can trigger the dispenser 102 to dispense a tracer test load in preparation or responsive to collection of a bioaerosol sample. In particular, in this implementation, the dispenser 102 can include a dispenser communication module 120 configured to receive commands for operation of the dispenser 102, such as from a controller (e.g., of the air sampler 104, of the dispenser 102, and/or of a second dispenser 102 installed in the space) configured to coordinate operation of the dispenser 102 and the air sampler 104.

Additionally, the system can include multiple dispensers 102 deployed throughout a facility, such as deployed to different rooms within a facility or deployed to a single room within the facility. The air sampler 104 can directly sample air from this environment and locally (and/or remotely) implement pathogen and/or barcode detection.

The dispenser 102 is described as configured to output tracer test loads containing DNA barcodes. However, the dispenser 102 can be configured to output tracer test loads containing any other tracer molecule, such as a fluorescent molecule, a fragrance and/or any other non-genetic molecule.

5.1 Housing

The dispenser 102 can include a dispenser housing 110 (hereinafter "housing 110") defining a body or "chassis": configured to support and locate a combination of dispenser 102 modules, a controller, and/or a communication module 120; configured for transport within a facility—including the particular environment—for reinstallation at a different location within the facility or within a remote facility (e.g., a laboratory) for maintenance and/or reassembly; configured to install in the particular environment (e.g., an office, a classroom, a restaurant) with minimal disruption to the particular environment; and configured to enable replacement of components or modules contained within the housing 110. For example, the housing 110 can define a rigid body including features for: fixing to a wall, setting on a surface (e.g., a surface of a table), or coupling within an electrical outlet within the particular environment; transport within the facility; and enabling access to components contained within the housing 110.

The housing 110 can include an outlet configured to pass tracer test loads from within the dispenser 102 (e.g., within the loading vessel 117) into the external environment. Further, the dispenser 102 can include a sprayer 118—arranged within or proximal the outlet—configured to transform volumes of the tracer test load into an array of particle-sized droplets of the tracer test load (e.g., barcodes in aqueous solution). Therefore, when released, these droplets (or "aerosolized particles") can each move independently throughout the space (e.g., based on barcode characteristics and/or environmental factors), thereby mimicking flow or dispersion of pathogens within the space. In one implementation, the dispenser 102 includes a nebulizer configured to convert a volume of the tracer test load into a corpus of aerosolized droplets.

The housing 110 can also include a set of doors to access various modules and/or components of the dispenser 102. In one implementation, the housing 110 can include a first door configured to enable access to the cartridge receptacle 112, such that a user may open (e.g., outward or inward) the door to insert and/or remove a cartridge 130 between dispense cycles. For example, to insert the cartridge 130 into the dispenser 102, the user may: align the cartridge 130 with the first door; and depress the door, by pushing the cartridge 130 through the door, to locate the cartridge 130 within the cartridge receptacle 112. Additionally and/or alternatively, in another implementation, the dispenser 102 can include a second door configured to enable access to the fluid reservoir 140, such that a user may open the second door to insert, remove, and/or refill the fluid reservoir 140 between dispense cycles.

5.2 Fluid Reservoir

The dispenser 102 can include a fluid reservoir 140 loaded with a volume of an aqueous solution (e.g., an amount of salt dissolved in a volume of purified water) configured to be mixed with barcode samples loaded into the dispenser 102. In particular, the fluid reservoir 140 can be loaded with an aqueous solution exhibiting a particular concentration of salt dissolved within a volume of water, such that the aqueous solution exhibits a set of properties configured to enable dispensation of tracer test loads—including barcodes mixed with volumes of the aqueous solution—at particular droplet sizes and/or concentrations of barcodes. Highly-concentrated barcode samples—stored in the cartridge 130—can thus be diluted within a volume of the aqueous solution stored in the fluid reservoir 140, such as prior to a dispense period.

The dispenser 102 can be reloaded with the aqueous solution over time—such as between dispense cycles—to continue releasing tracer test loads in the space. In one implementation, the fluid reservoir 140 can be refilled over time to replenish the aqueous solution within the fluid reservoir 140, such as manually by a user. For example, a user may access the fluid reservoir 140 (e.g., via a door on the housing 110) to load a volume of the aqueous solution into the fluid reservoir 140 (e.g., up to a defined fill level for the fluid reservoir 140. In one example, the user may access a supply of the aqueous solution to refill the fluid reservoir 140, such as a bulk volume of the aqueous solution or a pre-aliquoted volume of the aqueous solution.

Alternatively, in another implementation, the fluid reservoir 140 can be replaced over time to replenish the aqueous solution within the dispenser 102, such as manually by a user. In this implementation, the dispenser 102 can include a reservoir receptacle 114 configured to receive and rigidly locate the fluid reservoir 140—pre-loaded with a particular volume of the aqueous solution—within the dispenser 102.

For example, the fluid reservoir 140 can be configured to seat within the reservoir receptacle 114 external the housing no.

The system can alert the user to refill the fluid reservoir 140 in response to the volume of the aqueous solution falling below a threshold volume. For example, the dispenser 102 can include a sensor—facing the fluid reservoir 140—configured to detect a fill level of the fluid reservoir 140. The controller can interpret this fill level and selectively prompt a user associated with the space to refill the fluid reservoir 140 in response to the fill level falling below a threshold fill level. Alternatively, in another example, the controller can track: a quantity of dispense cycles executed by dispenser 102; and a dispense volume of the aqueous solution dispensed during each dispense cycle. The controller can then: access an initial volume of the aqueous solution loaded in the fluid reservoir 140; estimate a remaining volume of the aqueous solution loaded in the fluid reservoir 140 based on the initial volume, the quantity of dispense cycles, and the dispense volume for each dispense cycle; and, in response to the remaining volume falling below a threshold volume, prompt a user associated with the space to refill the fluid reservoir 140.

The system can therefore generate prompts to refill or reload the fluid reservoir 140—such as in a particular dispenser 102 in a set of dispensers 102 installed throughout a facility—and transmit these prompts to a user or users associated with the facility. Additionally and/or alternatively, in one variation, the dispenser 102 can include a set of user feedback controls arranged on an exterior of the housing no. For example, the dispenser 102 can include a light (e.g., a red light)—located on the housing 110—configured to pulse on and off responsive to detecting low volumes of the aqueous solution in the dispenser 102.

5.2.1 Loading Vessel

In one implementation, the dispenser 102 can include a loading vessel 117 fluidly coupled to the fluid reservoir 140 and configured to receive a particular volume of the aqueous solution from the fluid reservoir 140 for mixing with a barcode sample or barcode samples received from the cartridge 130, thereby generating a volume of a tracer test load. The loading vessel 117 can be fluidly coupled to the outlet and sprayer 118, such that the resulting tracer test load can be aerosolized and released into the surrounding environment.

In particular, in this implementation, the dispenser 102 can include: a fluid reservoir 140 loaded with a volume of the aqueous solution (e.g., a saline solution); a loading vessel 117 fluidly coupled to the fluid reservoir 140 and configured to mix barcode samples with volumes of the aqueous solution; and a fluid doser configured to dispense a set volume (e.g., one milliliter, five milliliters, ten milliliters) of the aqueous solution from the fluid reservoir 140 into the loading vessel 117. Additionally, in this implementation, the dispenser 102 can include a cleaning module (e.g., a UV-light) configured to sanitize surfaces of the loading vessel 117 between dispense cycles.

Additionally, the dispenser 102 can include an array of loading vessels 117 fluidly coupled to the fluid reservoir 140, such that multiple tracer test loads can be prepared simultaneously.

Alternatively, in another implementation, the dispenser 102 can include the fluid reservoir 140 including an array of loading vessels 117, each loading vessel 117 in the array of loading vessels 117, pre-loaded with a particular volume of the aqueous solution. In this implementation, the fluid reservoir 140 can be divided (e.g., via interior walls of the fluid reservoir 140) into an array of loading vessels 117, each loading vessel 117 in the array of loading vessels 117 fluidly decoupled from each other loading vessel 117. For example, the dispenser 102 can include a fluid reservoir 140 including: a first loading vessel 117 pre-loaded with a first subvolume of the aqueous solution; a second loading vessel 117 pre-loaded with a second subvolume of the aqueous solution; a third loading vessel 117 pre-loaded with a third subvolume of the aqueous solution; and a fourth loading vessel 117 pre-loaded with a fourth subvolume of the aqueous solution. In this example, each subvolume of the aqueous solution can be physically separated from each other volume of the aqueous solution contained in the fluid reservoir 140, such as via a set of interior walls forming the array of loading vessels 117 of the fluid reservoir 140.

6. Dispenser Cartridge

The system includes a dispenser cartridge 130 (hereinafter a "cartridge 130") configured to couple with the dispenser 102 to release concentrated tracer samples (e.g., barcode samples, fluorescence samples), stored in the cartridge 130, into the loading vessel 117 for dispensation of tracer test loads—including barcodes and/or fluorescent material mixed in volumes of the aqueous solution stored in the fluid reservoir 140—into the external environment.

In particular, in one implementation, the cartridge 130 can include: a set of tracer reservoirs 132 loaded with a set of barcode samples (e.g., highly-concentrated barcode samples); and a connector configured to transiently engage with the cartridge receptacle 112, to locate the set of tracer reservoirs 132 within the dispenser 102 (e.g., in a particular position). The cartridge 130 can be inserted into the dispenser 102 prior to initiation of a dispense cycle during which a sequence of tracer test loads is released into the exterior environment. The cartridge 130 can then be removed from the dispenser 102—such as upon completion of the dispense cycle or a set of dispense cycles—and replaced with a new cartridge 130 for dispensation of a next sequence of tracer test loads from the dispenser 102. Therefore, the system can include a set of cartridges 130. Each cartridge 130, in the set of cartridges 130, can be configured to include identical and/or unique barcode samples.

For example, the pathogen detection system 100 can include: a first cartridge 130 configured to transiently install within the dispenser housing no to supply DNA barcodes and/or fluorescent material to the dispenser 102 for dispensation of genetic test loads during a first time period; and a second cartridge 130 configured to transiently install within the dispenser housing 110 to supply DNA barcodes and/or fluorescent material to the dispenser 102 for dispensation of genetic test loads during a second time period (e.g., offset the first time period). Each cartridge 130, in the set of cartridges 130, can therefore be replaced over time (e.g., by a user associated with the space) in order to replenish the supply of tracer molecules (e.g., DNA barcodes and/or fluorescent material) for dispensation by the dispenser 102 and/or to replace types (e.g., size, identity, barcodes and/or fluorescent material) of tracer molecules loaded in the dispenser 102.

The cartridge 130 can be configured for handling by a user (e.g., a non-skilled user), such that the user may physically manipulate the cartridge 130 to locate the cartridge 130 within the cartridge receptacle 112 and enable release of barcode samples contained in the array of tracer reservoirs 132 into the loading vessel 117. The cartridge 130 can therefore be configured to serve as a housing for the set of barcode samples.

6.1 Tracer Reservoir

The cartridge 130 can include a set of tracer reservoirs 132, each tracer reservoir 132 loaded with a particular barcode sample, in a set of barcode samples. Each barcode sample, in the set of barcode samples, can define a particular initial barcode concentration such that, when the barcode sample is mixed with a volume of the aqueous solution in the loading vessel 117, the resulting tracer test load exhibits a target barcode concentration (e.g., less than the initial barcode concentration).

In one implementation, the cartridge 130 can include a single tracer reservoir 132 loaded with a single barcode sample. For example, the cartridge 130 can include a tracer reservoir 132 loaded with a barcode sample including: a first concentration of a first barcode of a first type (e.g., within a first size range); a second concentration of a second barcode of a second type (e.g., within a second size range); and a third concentration of a third barcode of a third type (e.g., within a third size range). Alternatively, in another example, the cartridge 130 can include a tracer reservoir 132 loaded with a barcode sample including a concentration of a (single) barcode (e.g., a generic barcode).

Alternatively, in another implementation, the cartridge 130 can include an array of tracer reservoirs 132 loaded with an array of barcode samples. For example, the cartridge 130 can include: a first tracer reservoir 132 loaded with a first barcode sample; a second tracer reservoir 132 loaded with a second barcode sample; a third tracer reservoir 132 loaded with a third barcode sample; etc. In this example, each barcode sample, in the array or barcode samples, can include known concentrations of barcodes of one or more barcode types.

In particular, each barcode sample can be configured to include a set of barcodes (e.g., of a set of barcode types). For example, the first barcode sample can include: a first concentration of a first barcode of a first barcode type; a second concentration (e.g., equivalent or distinct from the first concentration) of a second barcode of a second barcode type; a third concentration of a third barcode of a third barcode type. Alternatively, in another example, each barcode sample, in the array of barcode samples, can be configured to include a known concentration of a particular barcode (e.g., of a particular barcode type), such that the first barcode sample includes a known concentration of a first barcode and the second barcode sample includes a known concentration of a second barcode. Thus, each barcode sample, in the array of barcode samples loaded in the cartridge 130, can be configured to include varying concentrations and/or combinations of barcodes.

The dispenser 102 and cartridge 130 can be configured to enable dispensation of barcode samples—contained within the set of tracer reservoirs 132—into the loading vessel 117. In one implementation, the barcode sample can be loaded in a capsule—defining the tracer reservoir 132—loaded within the cartridge 130. The cartridge 130 can be configured to release this capsule into the loading vessel 117 for mixing with the aqueous solution. For example, the capsule (or "barcode capsule") can be configured to dissolve in the aqueous solution to release the barcode sample into the aqueous solution. In this implementation, the cartridge 130 can be loaded with an array of barcode capsules containing barcode samples. These barcode capsules can be located in particular slots within the cartridge 130, such that the system can selectively trigger release of particular barcode capsules from the cartridge 130.

Alternatively, in another implementation, the barcode sample can be loaded in a blister reservoir defining the tracer reservoir 132. In this implementation, the dispenser 102 can include a plunger arranged adjacent the tracer reservoir 132 (e.g., a blister reservoir) and configured to pierce (e.g., penetrate) the blister reservoir to release the concentrated barcode sample from within the blister reservoir and into the loading vessel 117. In one example, the controller can selectively actuate the plunger to locate the plunger over a particular tracer reservoir 132, in the set of tracer reservoirs 132. In this example, the dispenser 102 can include a fluid accumulator configured to collect fluid (i.e., barcode sample fluid) released from the tracer reservoir 132 and direct this fluid toward the loading vessel 117. Alternatively, in this example, the cartridge receptacle 112 can be configured to locate the tracer reservoir 132 and/or cartridge 130 over or within the loading vessel 117, such that when the plunger pierces the tracer reservoir 132, releasing fluid from the tracer reservoir 132, the loading vessel 117 directly collects the released fluid (i.e., barcode sample).

6.1.1 Variation: Pre-Mixed Barcode Samples

In one variation, the cartridge 130 can be loaded with a prepared tracer test load including a known concentration of barcodes in a volume of the aqueous solution. In this variation, the dispenser 102 can exclude the fluid reservoir 140 and/or the loading vessel 117. Therefore, upon insertion of the cartridge 130 into the dispenser 102, the dispenser 102 can automatically dispense volumes of the tracer test load (e.g., via the sprayer 118)— directly from the cartridge 130—at a particular frequency until the cartridge 130 is empty. A user may then dispose of this cartridge 130 and insert a new cartridge 130 loaded with a new tracer test load including identical and/or distinct concentrations of barcodes as the previous tracer test load.

Additionally and/or alternatively, in this variation, the dispenser 102 can be configured to receive multiple cartridges 130 simultaneously, in order to increase a duration between replacement of cartridges 130, thereby limiting an amount of user intervention required.

7. Tracking Barcode Dispensation

The system can track characteristics of tracer test loads released by the dispenser 102 over time. In particular, for each tracer test load, the system (e.g., the dispenser 102, the controller, the remote computer system) can track: an identity (e.g., DNA sequence) of each barcode contained in the tracer test load; an amount of each barcode; a volume of the aqueous solution; a concentration of each type (e.g., size, identity) of barcode; a size of each barcode; and/or a time of dispensation. The system can then store this information (e.g., in a remote database) in a profile generated for the tracer test load. The system can then access this profile to extract insights regarding airflow patterns in the space, detectability of pathogens in the space, dynamic range of the air sampler 104, etc., based on detected barcodes in bioaerosol samples collected by the air sampler 104.

In one example, the dispenser 102 can include a set of cartridges 130 (e.g., replaceable cartridges 130), each cartridge 130 in the set of cartridges 130 loaded with a particular set of barcode samples and labelled with a unique identifier—such as a QR code—linked to the cartridge 130. In this example, a first cartridge 130, in the set of cartridges 130, can include a QR code affixed to an exterior surface of the cartridge 130. The cartridge 130 can include: a first barcode sample—including barcodes of a first size, a first identity, and a first concentration—loaded in a first tracer reservoir 132 linked to a first position identifier; a second barcode sample—including barcodes of a second size, a second identity, and a second concentration—loaded in a second tracer reservoir 132 linked to a second position identifier; and a third barcode sample—including barcodes of a third size, a third identity, and a third concentration—loaded in a third tracer reservoir 132 linked to a third position identifier. The system can store each of these position identifiers—linked to the QR code affixed to the first cartridge 130—and corresponding barcode sample data (e.g., identity, size, concentration) in a remote database. Then, upon insertion of the first cartridge 130 into the dispenser 102, a sensor (e.g., a scanner) can record the QR code affixed to the cartridge 130 and a current timestamp.

In this example, the system (e.g., the remote computer system, the controller) can then trigger release of the first barcode sample—loaded in the first tracer reservoir 132—into the loading vessel 117. The system can then: generate a first profile for a first tracer test load; identify the first barcode sample based on the QR code and the first position identifier; and update the first profile to include the first barcode sample. Then, in response to releasing a first tracer test load—containing barcodes of the first barcode sample in solution—into the space, the system can update the first profile to include a timestamp and/or time period of dispensation of the first tracer test load. The system can then store this first profile, in a set of profiles, in the remote database.

Later, in response to detecting an amount of barcodes of a first size and a first identity (i.e., barcode sample data) in a bioaerosol sample collected by an air sampler 104 installed in the space, the system can: access the remote database; identify the first bioaerosol sample based on the first size and the first identity; and access the first profile for the first tracer test load. The system can then leverage the timestamp corresponding to release of the first tracer test load to extract insights related to detectability, flow, and/or dispersion of barcodes of the first size and the first identity—and therefore similar airborne particles more generally—in the space over time, such as related to bioaerosol clearance rate and/or exposure reduction rate.

The system can similarly track other types of tracer molecules—such as a fluorescent molecule, a fragrance and/or any non-genetic molecule—released by a dispenser 102 or dispensers 102 in the space, based on known characteristics of these tracer molecules, in order to derive insights related to detectability, flow, and/or dispersion of tracer molecules and/or aerosols more generally in this space.

7.1 Single Tracer Molecule: Multiple Barcode Identifiers

In one implementation, the dispenser 102 can be configured to output genetic test loads containing tracer molecules including one or more barcodes—containing identifying information linked to a particular tracer molecule or group of tracer molecules—encoded within a single strand of DNA. Later, in response to detection of these barcodes in bioaerosol samples collected by the air sampler 104, the system can thus: link barcodes detected in bioaerosol samples to specific tracer test loads—such as dispensed at a particular time and/or by a particular dispenser 102 (e.g., installed in a particular location within a facility)—based on known (or recorded) dispense schedules of tracer test loads containing these barcodes; and therefore derive insights related to air flow patterns in this space—such as air flow rate, air flow direction, air flow velocity, bioaerosol clearance rate, bioaerosol exposure reduction rate, etc.—based on time and/or location of dispensation of these tracer molecules by the dispenser 102 and time and/or location of collection of these tracer molecules by the air sampler 104.

7.1.1 Barcode Identifier: Location

In one implementation, the system can link tracer molecules detected in bioaerosols collected by the air sampler 104 to a particular location within a facility and/or to a particular dispenser 102 (e.g., installed in a particular location).

For example, the system can include a first dispenser 102—located in a first location within a facility—loaded with a first dispenser cartridge 130 130. The first dispenser cartridge 130 130 can be loaded with a first tracer sample containing a first set of tracer molecules (e.g., barcodes). In this example, the first set of tracer molecules can include a first tracer molecule including: a first randomized genetic sequence (i.e., a randomized barcode)—unique to this first tracer molecule—encoded on a DNA strand of the first tracer molecule; and a first predefined (e.g., nonrandomized) genetic sequence (i.e., a predefined barcode)—common to the first set of tracer molecules in the first tracer sample loaded in the dispenser cartridge 130 130— encoded on the DNA strand adjacent (e.g., upstream, downstream, contiguous) the first randomized genetic sequence. Additionally, the first set of tracer molecules can include a second tracer molecule including: a second randomized genetic sequence—unique to this second tracer molecule—encoded on a DNA strand of the second tracer molecule; and the first predefined genetic sequence encoded on the DNA strand of the second tracer molecule adjacent (e.g., upstream, downstream, contiguous) the second randomized genetic sequence. Similarly, the first set of tracer molecules can include a third tracer molecule, a fourth tracer molecule, a fifth tracer molecule, etc., each tracer molecule, in the first set of tracer molecules, including a randomized genetic sequence—unique to the particular tracer molecule—and the first predefined genetic sequence common to the first set of tracer molecules.

In this example, the system can: at a first time, trigger dispensation of a tracer test load—containing the first set of tracer molecules—from the dispenser 102; and (approximately) simultaneously—and/or preceding or immediately succeeding dispensation of the tracer test load—trigger initiation of a sampling period by the air sampler 104 to trigger collection of a bioaerosol sample. Then, in response to detecting the first predefined genetic sequence in bioaerosols collected by the air sampler 104 (e.g., travelling through the tunnel 152 and/or collected in the bioaerosol sample), the system can automatically link these collected bioaerosols to the tracer test load—containing the first set of tracer molecules—dispensed by the dispenser 102 at the first time. Further, the system can then access a total quantity of (unique) randomized genetic sequences—linked to the first predefined genetic sequence—detected in bioaerosols collected by the air sampler 104 during this sampling period, in order to estimate a proportion of tracer molecules, in the first set of tracer molecules, collected by the air sampler 104, and thereby derive insights related to air flow in this space based on this proportion.

Additionally, in the preceding example, the pathogen detection system can include a second dispenser 102—installed in a second location distinct from the first location within the facility—loaded with a second dispenser cartridge 130 130. The second dispenser cartridge 130 130 can be loaded with a second tracer sample containing a second set of tracer molecules. The second set of tracer molecules can include a third tracer molecule including: a third randomized genetic sequence—unique to this third tracer molecule—encoded on a DNA strand of the third tracer molecule; and a second predefined (e.g., nonrandomized) genetic sequence (i.e., a predefined barcode)—common to the second set of tracer molecules in the second tracer sample loaded in the second dispenser cartridge 130 130— encoded on the DNA strand adjacent the third randomized genetic sequence.

In this example, the system can thus: at a first time, trigger dispensation of the tracer test load—containing the first set of tracer molecules—from the dispenser 102 installed in the first location; at approximately the first time, trigger dispensation of a second tracer test load—containing the second set of tracer molecules—by the second dispenser 102 installed in the second location; trigger initiation of the sampling period by the air sampler 104 to trigger collection of a bioaerosol sample. Then, in response to detection of the first predefined genetic sequence in bioaerosols collected by the air sampler 104, the system can link detection of these bioaerosols to the first tracer test load—containing the first set of tracer molecules—dispensed by the dispenser 102 at the first location and at the first time. Additionally and/or alternatively, in response to detection of the second predefined genetic sequence in bioaerosols collected by the air sampler 104, the system can link detection of these bioaerosols to the second tracer test load—containing the second set of tracer molecules—dispensed by the second dispenser 102 at the second location at the first time.

7.1.2 Barcode Identifier: Time

Additionally and/or alternatively, in another implementation, the system can link tracer molecules detected in bioaerosols collected by the air sampler 104 to a particular time (e.g., time value, timestamp, time period) associated with release of a tracer test load containing these tracer molecules.

For example, the system can include a dispenser 102 loaded with a dispenser cartridge 130. The dispenser cartridge 130 can be loaded with: a first tracer sample containing a first set of tracer molecules (e.g., barcodes); and a second tracer sample containing a second set of tracer molecules (e.g., barcodes). In this example, each tracer molecule, in the first set of tracer molecules, can be configured to include: a randomized genetic sequence (i.e., a randomized barcode)—unique to the tracer molecule—encoded on a DNA strand of the tracer molecule; and a first predefined (e.g., nonrandomized) genetic sequence (i.e., a predefined barcode)—common to the first set of tracer molecules in the first tracer sample loaded in the dispenser cartridge 130— encoded on the DNA strand adjacent (e.g., upstream, downstream, contiguous) the randomized genetic sequence. Further, each tracer molecule, in the second set of tracer molecules, can be configured to include: a randomized genetic sequence—unique to the tracer molecule—encoded on a DNA strand of the tracer molecule; and a second predefined genetic sequence—common to the second set of tracer molecules in the second tracer sample—encoded on the DNA strand of the tracer molecule adjacent (e.g., upstream, downstream, contiguous) the second randomized genetic sequence.

In the preceding example, the system can thus: at a first time, trigger initiation of a sampling period by the air sampler 104 to trigger collection of a bioaerosol sample; at a first time during the sampling period, trigger dispensation of a first tracer test load—containing the first set of tracer molecules—from the dispenser 102; and, at a second time succeeding the first time, trigger dispensation of a second tracer test load—containing the second set of tracer molecules—by the dispenser 102. Then, in response to detection of the first predefined genetic sequence in bioaerosols collected by the air sampler 104, the system can link detection of these bioaerosols to the first tracer test load—containing the first set of tracer molecules—dispensed by the dispenser 102 at the first time. Additionally and/or alternatively, in response to detection of the second predefined genetic sequence in bioaerosols collected by the air sampler 104, the system can link detection of these bioaerosols to the second tracer test load—containing the second set of tracer molecules—dispensed by the dispenser 102 at the second time. The system can therefore delineate between detection of bioaerosols released at different times by the dispenser 102, and thereby derive insights related to time and bioaerosol detection, such as a velocity of bioaerosols travelling between the dispenser 102 and the air sampler 104 and/or a bioaerosol clearance rate for all bioaerosols and/or bioaerosols of a particular type in this space.

8. Fluorescent Tracer Molecules

In one variation, the dispenser 102 can be configured to release tracer test loads containing fluorescent tracer molecules (e.g., fluorescent material). In particular, in this variation, the dispenser 102 can be configured to receive a dispenser cartridge 130 containing fluorescent material (e.g., fluorescent molecules) in solution. Once loaded with the cartridge 130, the dispenser 102 can be configured to release tracer test loads—including known amounts of fluorescent material (e.g., released from the dispenser cartridge 130) in known volumes of the aqueous solution (e.g., dispensed from the fluid reservoir 140)—at controlled frequencies, as described above.

In this variation, the dispenser 102 can include a dispenser cartridge 130 including a set of tracer reservoirs 132 containing fluorescent material in solution. Therefore, the actuator 116 can be configured to selectively release fluorescent material from the set of tracer reservoirs 132 (e.g., based on commands received by the dispenser communication module 120) for mixing with fluid released from the fluid reservoir 140 and/or for dispensation by the dispenser 102. Further, in this variation, the set of tracer reservoirs 132 can contain fluorescent material and/or DNA barcodes in solution. Additionally and/or alternatively, in a similar variation, the dispenser 102 can include a dispenser cartridge 130 including a set of tracer reservoirs 132 including: a set of barcode reservoirs 132 containing DNA barcodes in solution; and a set of fluorescence reservoirs 132 containing fluorescent material in solution. In this variation, the actuator 116 can be configured to selectively release solution from the set of barcode reservoirs 132 and/or the set of fluorescence reservoirs 132 (e.g., based on the command received by the dispenser communication module 120).

In this variation, the pathogen detection system can be configured to detect fluorescence (e.g., intensity of fluorescence) of bioaerosols in air collected by the air sampler 104. For example, the air sampler 104 can include a fluorescence detector 154— such as an optical sensor (e.g., a fluorescence reader)—configured to measure fluorescence in bioaerosols collected by the air sampler 104. In this example, the air sampler 104 can include a fluorescence detector 154 arranged within the tunnel 152 of the air sampler 104 and configured to record fluorescence signals emitted by these bioaerosols, such as in (near) real time as these bioaerosols flow through the tunnel 152. The system (e.g., a remote computer system or a local controller) can then: read these fluorescence signals recorded by the fluorescence detector 154; and interpret presence (e.g., magnitude) of fluorescent molecules travelling through the tunnel 152 of the air sampler 104 based on these fluorescence signals.

Alternatively, in a similar example, the air sampler 104 can include a fluorescence detector 154 arranged proximal the collector plate of the sampler cartridge 160 and configured to record fluorescence signals emitted by bioaerosols collected on the collector plate.

8.1 Tracking Fluorescent Material

In the preceding variation, the system can track characteristics of tracer test loads—containing fluorescent material in solution—released by the dispenser 102 over time. In particular, for each tracer test load released by a set of dispenser 102 (e.g., a single dispenser 102, multiple dispensers 102), the system can track: an amount of fluorescent material (or "fluorescence level") contained in each tracer test load; a volume of fluid (or "solution") of the tracer test load; a type or types of fluorescent material contained in the tracer test load, such as a red-, yellow-, and/or green-fluorescent material; a size of each fluorescent molecule or particle in the tracer test load; a time of dispensation of the tracer test load; and/or a location of dispensation of the tracer test load (e.g., a location of the dispenser 102 during dispensation of the tracer test load). Based on these tracked characteristics, the system can then leverage detection of fluorescent material—exhibiting these characteristics—at the air sampler 104 to derive insights related to flow and/or distribution of aerosols (e.g., bioaerosols such as pathogens and/or tracer molecules) in this particular space.

In one implementation, the system can associate fluorescent material detected at the air sampler 104 to a particular tracer test load dispensed by a particular dispenser 102, in a set of dispensers 102, installed in an indoor environment. In this implementation, the pathogen detection system 100 can include: a set of dispensers 102 installed at a set of locations within the indoor environment; and an air sampler 104 (or a set of air samplers 104) installed within the indoor environment (e.g., at a target location within the indoor environment). Each dispenser 102, in the set of dispensers 102, can be configured to release tracer test loads containing fluorescent material linked to the dispenser 102 and/or location of the dispenser 102.

For example, the pathogen detection system 100 can include: a first dispenser 102 installed in a first location within an indoor (or "enclosed") environment; and a second dispenser 102 installed in a second location within the indoor environment. In this example, the first dispenser 102 can include: a first dispenser cartridge 130 containing fluorescent material of a first type (e.g., red-fluorescent material) and/or DNA barcodes in solution; a first dispenser communication module 120 configured to receive commands for operation of the first dispenser 102; and a first actuator 116 configured to release a first solution dose (e.g., of fluorescent material of the first type) from the first dispenser cartridge 130 based on a first command received by the first dispenser communication module 120. The second dispenser 102 can include a second dispenser cartridge 130 containing fluorescent material of a second type (e.g., green-fluorescent material) and/or DNA barcodes in solution; a second dispenser communication module 120 configured to receive commands for operation of the second dispenser 102; and a second actuator 116 configured to release a second solution dose (e.g., of fluorescent material of the first type) from the second dispenser cartridge 130 based on a second command received by the second dispenser communication module 120.

In the preceding example, the system can: trigger dispensation of a first tracer test load—containing fluorescent material of the first type and/or DNA barcodes in solution—by the first dispenser 102 at the first location at a first time, such as via output of a first command to the first dispenser communication module 120; and trigger dispensation of a second tracer test load—containing fluorescent material of the second type and/or DNA barcodes in solution—by the second dispenser 102 at the second location at approximately the first time, such as via output of a second command to the second dispenser communication module 120. Prior and/or approximately concurrent dispensation of the first and second tracer test loads, the system can also trigger collection of a bioaerosol sample by the air sampler 104.

Then, in the preceding example, in response to detecting presence of fluorescent material of the first type (e.g., red-fluorescent material) at the air sampler 104, the system can automatically associate a time of detection, a detected fluorescence level (e.g., amount of fluorescent material, intensity of fluorescence) of fluorescent material of the first type, and/or a location of detection (e.g., a location of the air sampler 104) with the first tracer test load released at the first time and by the first dispenser 102 installed in the first location in the space. Additionally and/or alternatively, in this example, in response to detecting presence of fluorescent material of the second type (e.g., green-fluorescent material) at the air sampler 104, the system can automatically associate time of detection, detected fluorescence level, and/or location of detection of fluorescent material of the second type with the second tracer test load released at the first time and by the second dispenser 102 installed in the second location in the space. The system can therefore derive insights related to detectability, flow, and/or dispersion of tracer molecules (and/or aerosols more generally) in this space at increased specificity by enabling detection and identification of tracer molecules dispensed in both the first and second locations (and/or any other location of a dispenser 102 in the set of dispensers 102).

Additionally and/or alternatively, in a similar implementation, the system can associate fluorescent material detected at the air sampler 104 to a particular tracer test load dispensed by the dispenser 102 at a particular time (e.g., time of day, time value, timepoint). For example, the dispenser 102 can include a dispenser cartridge 130 including a set of reservoirs (or "tracer reservoirs 132") containing fluorescent material configured for dispensation by the dispenser 102. In particular, in this example, the dispenser 102 can include: a first reservoir containing fluorescent material of a first type (e.g., exhibiting a first fluorescence signature) configured for dispensation by the dispenser 102 at a first time; and a second reservoir containing fluorescent material of a second type (e.g., exhibiting a second fluorescence signature distinct from the first fluorescence signature) configured for dispensation by the dispenser 102 at a second time. The system can then: trigger dispensation of a first tracer test load—containing fluorescent material of the first type (e.g., released from the first reservoir by the actuator 116)— by the dispenser 102 at approximately the first time; trigger dispensation of a second tracer test load—containing fluorescent material of the second type (e.g., released from the second reservoir by the actuator 116)— by the dispenser 102 at approximately the second time. Then, in response to detection of fluorescent material of the first type at the air sampler 104 (e.g., via an optical sensor arranged within the air sampler 104), the system can associate this detected fluorescent material with the first tracer test load dispensed at the first time. Additionally and/or alternatively, in response to detection of fluorescent material of the second type at the air sampler 104, the system can associate this detected fluorescent material of the second type with the second tracer test load dispensed at the second time.

9. Calibration

During a calibration period, the system can run evaluations to calibrate and confirm functionality of the dispenser 102 and/or air sampler 104. In particular, the system can:

trigger the dispenser 102 to intermittently (e.g., at a fixed frequency, pseudo-randomly) release tracer test loads into a space; trigger the air sampler 104 to collect bioaerosol samples during and/or after release of these tracer test loads in the space; detect barcode levels of various barcodes contained in these tracer test loads via genetic sequencing of bioaerosol samples collected by the air sampler 104; and compare detected barcode levels with actual or known barcode levels in the tracer test loads to identify a calibration factor for this air sampler 104.

The system can store information collected for a space during the calibration period in a calibration profile for this space. Later, during a live period succeeding the calibration period, the system can access this calibration profile for the space to: predict pathogen levels within the space; detect changes (e.g., environmental changes) within the space; and provide recommendations to users associated with the space to improve detectability of pathogens in the space.

9.1.1 One Air Sampler+One Dispenser: Single Space

In one implementation, the system can include: an air sampler 104 deployed in a space (e.g., an office room, a classroom, a dining room in a restaurant); and a dispenser 102 deployed in the space. In this implementation, the system can identify a calibration factor for this space based on known quantities of barcodes output by the dispenser 102 and detected quantities of barcodes collected by the air sampler 104. The system can then leverage this calibration factor to more accurately predict quantities (or levels) of pathogens in a particular space based on bioaerosol samples collected by the air sampler 104.

For example, during a calibration period for a space including an air sampler 104 and a dispenser 102, the system can: at a first time, trigger collection of a first bioaerosol sample by the air sampler 104 over a first sampling window of a target duration (e.g., 1 minute, 1 hour, 24 hours); and, at a second time succeeding the first time within the fixed sampling window (e.g., seconds after the first time), trigger dispensation of a tracer test load by the dispenser 102, the tracer test load defining a first volume and exhibiting a first concentration of barcodes. Upon expiration of the first sampling window, the bioaerosol sample can be collected for further analysis via genetic testing, such as within a detection module within the air sampler 104 or at a remote location (e.g., a laboratory) distinct from the space. via genetic testing to identify a detected barcode level within the bioaerosol sample during the fixed sampling window. The system can then: access the detected barcode level (e.g., load, concentration) corresponding to a first barcode in the bioaerosol sample; calculate a true barcode level in the space based on the first volume and the first concentration of barcodes in the tracer test load; and calculate a calibration factor based on the detected barcode level in the bioaerosol sample and the true barcode level in the tracer test load. The system can then store this calibration factor in a calibration profile corresponding to this space.

Later, during a live period succeeding the calibration period, the system can leverage this calibration factor to predict pathogen levels in the space based on detected pathogen levels in bioaerosol samples collected by the air sampler 104. In particular, in the preceding example, the system can: access a detected pathogen level of a first pathogen in a bioaerosol sample collected by the air sampler 104 during a second sampling window of the target duration; access the calibration factor stored in the calibration profile corresponding to the space; and calculate a pathogen level of the first pathogen, in the space, during the second sampling window, based on the detected pathogen level and the calibration factor.

The system can calculate a single calibration factor for all barcodes in a tracer test load based on total amount of barcodes in the tracer test load and detected in the bioaerosol sample. Alternatively, the system can calculate a unique calibration factor for each type of barcode in the tracer test load. For example, the system can: calculate a first calibration factor for barcodes of a first barcode type (e.g., within a first size range); calculate a second calibration factor for barcodes of a second barcode type (e.g., within a second size range greater than the first size range); and calculate a third calibration factor for barcodes of a third barcode type (e.g., within a third size ranger greater than the second size range). Therefore, in this example, because these different barcodes can be linked to different pathogens (e.g., of similar sizes or behaviors), the system can apply these calibration factors to different pathogens, in a set of pathogens, detectable by the air sampler 104.

In particular, in the preceding example, the system can: calculate a first pathogen level for a first pathogen (e.g., exhibiting a size within the first size range) associated with the first barcode type based on a first detected pathogen level of the first pathogen in a bioaerosol sample and the first calibration factor; calculate a second pathogen level for a second pathogen (e.g., exhibiting a size within the second size range) associated with the second barcode type based on a second detected pathogen level of the second pathogen in the bioaerosol sample and the second calibration factor; and calculate a third pathogen level for a third pathogen (e.g., exhibiting a size within the third size range) associated with the third barcode type based on a third detected pathogen level of the third pathogen in the bioaerosol sample and the third calibration factor.

The system can derive this calibration factor (e.g., for a particular space) over multiple sampling windows during the calibration period. The system can therefore compile results obtained across multiple sampling periods to converge on a particular calibration factor or set of calibration factors (e.g., for a set of barcodes) for this space.

Further, in one variation, the system can derive multiple calibration factors for the space based on different locations of the air sampler 104 within the space. For example, the system can derive a first calibration factor for the air sampler 104 located in a first region (e.g., mounted to a first wall) within a space. Then, the system can prompt a user associated with the space to relocate the air sampler 104 to a second region (e.g., mounted to a second wall opposite the first wall) within the space for recalibration at the second region. The system can then derive a second calibration factor for the air sampler 104 located in the second region within the space. In this example, in response to the second calibration factor falling below the first calibration factor— such that a detected proportion of a true barcode load output by the dispenser 102 and detected at the air sampler 104 is greater at the second region—the system can: assign the air sampler 104 to the second region in the space; and prompt the user to maintain the air sampler 104 within the second region. Additionally and/or alternatively, the system can repeat this process for additional regions within the space to find a location within the space at which the air sampler 104 can detect a greatest proportion of the true barcode load output by the dispenser 102.

During the calibration period, the system can trigger the air sampler 104 to collect bioaerosol samples during sampling windows of a target duration matched to a duration of sampling windows during the live period to enable accurate prediction of pathogen levels within the space. Additionally and/or alternatively, the system can implement sampling windows of scalable durations and scale these calibration factors accordingly. For example, the system can derive a first calibration factor during a first sampling window of a first duration during the calibration period. Then, during a live period succeeding the calibration period, the system can: trigger collection of a bioaerosol sample during a sampling window of a second duration greater than the first duration; calculate a scaling factor based on the first duration and the second duration; derive a second calibration factor based on the scaling factor and the first calibration factor; access a detected pathogen level in the bioaerosol sample; and predict a first pathogen level in the bioaerosol sample based on the detected pathogen level and the second calibration factor.

9.1.2 One Air Sampler+Multiple Dispensers: Single Space

In one implementation, the system can include: an air sampler 104 deployed in a space; and a set of dispensers 102 deployed in the space. In this implementation, the system can similarly derive a set of calibration factors for this space based on known quantities of barcodes output by the dispenser 102 and detected quantities of barcodes collected by the air sampler 104. In particular, the system can derive a unique calibration factor for each dispenser 102, in the set of dispenser 102, in the space. The system can then leverage these calibration factors to identify regions of the space, in which the set of dispensers 102 are located, at which barcodes—and thereby pathogens—are more easily detected and to identify regions of the space in which barcodes are less detectable.

For example, the system can include: an air sampler 104 mounted to a first wall within a room; a first dispenser 102—configured to dispense quantities of a first barcode—mounted to second wall opposite the first wall and; a second dispenser 102—configured to dispense quantities of a second barcode—located on a desk bordering the first wall and a third wall; and a third dispenser 102—configured to dispense quantities of a third barcode—located on a window sill along a fourth wall opposite the third wall. Then, during a calibration period for the room, the system can: trigger collection of a bioaerosol sample by the air sampler 104 over a first sampling window of a target duration (e.g., 1 minute, 1 hour, 24 hours); trigger dispensation of a first tracer test load by the first dispenser 102, the first tracer test load defining a first volume and exhibiting a first concentration of the first barcode; trigger dispensation of a second tracer test load by the second dispenser 102, the second tracer test load defining a second volume (e.g., equivalent the first volume) and exhibiting a second concentration (e.g., equivalent the first concentration) of the second barcode; and trigger dispensation of a third tracer test load by the third dispenser 102, the third tracer test load defining a third volume (e.g., equivalent the first and second volume) and exhibiting a third concentration (e.g., equivalent the first and second concentration) of the third barcode. Then, upon expiration of the target duration, the bioaerosol sample can be collected (e.g., within the air sampler 104, at a remote location) for further analysis (e.g., via genetic testing) of the bioaerosol sample.

Upon completion of genetic testing of the bioaerosol sample, the system can: access a first detected barcode level of the first barcode in the bioaerosol sample; access a second detected barcode level of the second barcode in the bioaerosol sample; and access a second detected barcode level of the first barcode in the bioaerosol sample. The system can then: calculate a first true barcode level in the room based on the first volume and the first concentration of the first barcode in the first tracer test load; calculate a first detectable proportion of the first barcode based on the first detected barcode level and the first true barcode level; calculate a second true barcode level in the room based on the second volume and the second concentration of the second barcode in the second tracer test load; calculate a second detectable proportion of the second barcode based on the second detected barcode level and the second true barcode level; calculate a third true barcode level in the room based on the third volume and the third concentration of the third barcode in the third tracer test load; and calculate a third detectable proportion of the third barcode based on the third detected barcode level and the third true barcode level. In this example, in response to the third detectable proportion falling below a threshold proportion, the system can then prompt a user associated with the room to place a fan proximal the third dispenser 102 to increase air flow from the third region of the room toward the air sampler 104. Therefore, based on these detectable proportions, the system can identify regions of the room which can exhibit limited detectability of barcodes and/or pathogen and thereby suggest changes (e.g., environmental changes) within the room to improve detectability.

Further, in the preceding example, the system can: calculate a first calibration factor for the first dispenser 102 mounted to the second wall; calculate a second calibration for the second dispenser 102 located on the desk; and calculate a third calibration factor for the third dispenser 102 located in the window sill. The system can then calculate a total calibration factor for the room based on the first, second, and third calibration factors. The system can therefore account for varying distribution of bioaerosols (e.g., barcodes and/or pathogens) within the room due to environmental factors (e.g., airflow, geometry, occupancy) in this room.

Additionally, the system can prompt a user associated with the space to relocate the air sampler 104 within the space during the calibration period in order to increase detectability of barcodes and/or pathogens by the air sampler 104. For example, the system can: calculate a first total calibration factor for the air sampler 104 located in a first region of a space based on a first set of calibration factors corresponding to different dispensers 102 (e.g., at different locations within a space); calculate a second total calibration factor for the air sampler 104 located in a second region of the space based on a second set of calibration factors; and calculate a third total calibration factor for the air sampler 104 located in a third region of the space based on a third set of calibration factors. In response to the second total calibration factor exceeding the first and third total calibration factors, the system can then: assign the air sampler 104 to the second region within the space; and prompt a user associated with the space to return the air sampler 104 to the second region.

Further, the system can leverage a set of calibration factors, derived for a single space during a calibration period, to output ranges of (predicted) pathogen levels detected within the space. For example, during a calibration period, the system can derive: a first calibration factor of 120 percent corresponding to a dispenser 102 located in a first region of a room; a second calibration factor of 150 percent corresponding to a dispenser 102 located in a second region of the room; and, thereby, a calibration factor range of 120 percent to 150 percent. During a live period succeeding the calibration period, in response to detecting a first pathogen level of 500 colony-forming-units-per-cubic-meter, the system can then leverage the calibration factor range to estimate a pathogen level range between boo colony-forming-units-per-cubic-meter and 750 colony-forming-units-per-cubic-meter.

9.1.3 One Air Sampler+Multiple Dispensers: Multiple Spaces

In a similar implementation, the system can include: an air sampler 104 deployed in a first space, in a set of spaces, within a facility; and a set of dispensers 102 deployed throughout the set of spaces within the facility. Similarly, in this implementation, the system can derive a set of calibration factors for the set of spaces within the facility based on known quantities of barcodes output by the set of dispensers 102 and detected quantities of barcodes collected by the air sampler 104. In particular, the system can derive a unique calibration factor for each space, in the set of spaces, in the facility based on detected barcodes output by a dispenser 102, in the set of dispensers 102, located in each space.

For example, the system can include: an air sampler 104 located within a central space on a first floor of an office building; a first dispenser 102—configured to dispense quantities of a first barcode—located within a conference room on the first floor; a second dispenser 102—configured to dispense quantities of a second barcode—located within a cafeteria on the first floor; and a third dispenser 102—configured to dispense quantities of a third barcode—located within an office on the first floor. During a calibration period for the first floor, the system can: trigger collection of a bioaerosol sample by the air sampler 104 over a first sampling window; trigger dispensation of a first tracer test load by the first dispenser 102; trigger dispensation of a second tracer test load by the second dispenser 102; and trigger dispensation of a third tracer test load by the third dispenser 102. Upon completion of the sampling window and genetic testing of the bioaerosol sample, the system can: access a first detected barcode level of the first barcode, a second detected barcode level of the second barcode, and a third detected barcode level of the third barcode in the bioaerosol sample; and access a first true barcode level of the first barcode (e.g., based on a known concentration of the first barcode within the first tracer test load), a second true barcode level of the second barcode (e.g., based on a known concentration of the second barcode within the second tracer test load), and a third true barcode level of the third barcode (e.g., based on a known concentration of the third barcode within the third tracer test load). Then, the system can: calculate a first calibration factor for the conference room based on the first detected barcode level and the first true barcode level; calculate a second calibration factor for the cafeteria based on the second detected barcode level and the second true barcode level; and calculate a third calibration factor for the office based on the third detected barcode level and the third true barcode level.

Based on the first, second, and third calibration factors, the system can prompt a user (or users) associated with these spaces to: implement various environmental controls to improve detectability of barcodes and/or pathogens in spaces exhibiting relatively low detectability; and/or implement additional detection methods to enable detection of barcodes and/or pathogen in these spaces. For example, in response to the third calibration factor exceeding a threshold factor—such that the third detected barcode level is significantly lower than the third true barcode level—the system can: prompt a user associated with the space to install a fan proximal a doorway of the office to increase airflow toward the central room including the air sampler 104. The system can then trigger initiation of a second sampling window to recalibrate the air sampler 104. The system can then update the third calibration factor based on this increased airflow from the office. In this example, in response to the third calibration factor exceeding the threshold factor after installation of the fan, the system can prompt the user to implement surface testing (e.g., via test strips) of pathogens in the office to increase confidence of predicted pathogen levels within the office. Additionally and/or alternatively, the system can prompt the user to install a second air sampler 104 within the office and/or within any other spaces on the first floor to improve detection.

Further, in this implementation, the system can leverage a range of calibration factors derived for a set of spaces within a facility to predict a range of (predicted) pathogen levels within the facility. For example, during a calibration period, the system can derive: a first calibration factor (e.g., 5×) for a first space within a facility; and a second calibration factor (e.g., 50×) for a second space within the facility, the second calibration factor greater than the first calibration factor, such that barcodes originating from the second space are less detectable than barcodes originating from the first space. Then, during a live period succeeding the calibration period, in response to detecting a first pathogen level of 10 colony-forming-units-per-cubic-meter, the system can estimate a first pathogen level range of 50 colony-forming-units-per-cubic-meter to 500 colony-forming-units-per-cubic-meter. In this example, in response to an upper limit (e.g., 500 colony-forming-units-per-cubic-meter) of the first pathogen level range exceeding a threshold pathogen level, the system can prompt a user associated with the space to perform a surface test (e.g., via a test strip) in the second space. Then, in response to results of the surface test indicating a pathogen level below the threshold pathogen level, the system can update the first pathogen level accordingly and verify this sample as "safe." Alternatively, in response to results of the surface test indicating a pathogen level above the threshold pathogen level, the system can alert the user to implement a mitigation technique (e.g., cleaning technique, modification to occupancy, evacuation) matched to the pathogen level.

9.1.4 Variation: Continuous Sampling

In one variation, the air sampler 104 can be configured to continuously or semi-continuously collect bioaerosol samples from the space during a calibration period to generate a timeseries of barcode data during the calibration period. The system can then leverage this timeseries of barcode data to generate a calibration curve for this space.

For example, during a calibration period for a space, the system can: trigger collection of a first bioaerosol sample by an air sampler 104 installed in the space during a first sampling window of a target duration (e.g., 1 minute, 30 minutes, 1 hour) within the calibration period; trigger dispensation of a first tracer test load by a dispenser 102 installed in the space during the first sampling window; trigger collection of a second bioaerosol sample by the air sampler 104 during a second sampling window of the target duration, immediately succeeding the first sampling window, within the calibration period; and trigger collection of a third bioaerosol sample by the air sampler 104 during a third sampling window of the target duration, immediately succeeding the second sampling window, within the calibration period. Then, upon completion of analysis of these bioaerosol samples, the system can: access a first detected barcode level in the first bioaerosol sample; access a second detected barcode level in the second bioaerosol sample; and access a third detected barcode level in the third bioaerosol sample. The system can then leverage the first, second, and third detected barcode levels to generate a calibration curve representative of changes in levels of detected barcodes in the space over time. In particular, in this example, when the tracer test load is initially output by the dispenser 102 during the first sampling window, the system can detect a relatively low concentration of barcodes in the bioaerosol sample, represented by the first pathogen level, due to distance between the air sampler 104 and the dispenser 102. Alternatively, due to air flow or current within the space, the system can detect a relatively high concentration of barcodes in the second bioaerosol sample, represented by the second pathogen level. Then, as barcodes present in the first tracer test load settle and/or disperse within the space, the system can detect a relatively moderate concentration of the barcodes in the third bioaerosol sample, represented by the third pathogen level. The system can then interpolate between these detected barcode levels to generate the calibration curve for this space.

The calibration curve can therefore be leveraged to model movement of barcodes and/or pathogens within the space and changes in barcode and/or pathogen levels in air in this space over time. The system can derive a calibration curve for a particular space, a particular barcode, a particular barcode type (e.g., based on size), and/or a particular region (e.g., in which the air sampler 104 is located) within the space.

In particular, during a live period succeeding the calibration period, the system can compare a detected pathogen curve (in near real-time) to the calibration period for this space to predict current and/or future pathogen levels within this space. For example, during a live period in a space, the system can: access a first detected pathogen level in a first bioaerosol sample collected during a first sampling window; access a second detected pathogen level in a second bioaerosol sample collected during a second sampling window succeeding the first sampling window; access a third detected pathogen level in a third bioaerosol sample collected during a third sampling window succeeding the second sampling window; and derive a first detected pathogen curve for this space during the live period based on the first, second, and third pathogen levels. The system can then: access a calibration curve stored in a calibration profile for this space; characterize a correlation between the first detected pathogen curve and a first portion of the calibration curve; and, in response to the correlation exceeding a threshold correlation, predict a fourth pathogen level at a future time (e.g., within the 30 minutes, within the next hour, within the next day) based on first detected pathogen curve, the calibration curve, and the correlation.

10. Variation: Calibration Model

In one variation, the system can execute multiple calibration periods to construct a calibration model for the space as a function of environmental conditions within the space. In particular, the system can access environmental data (e.g., air temperature, humidity, time of day, indoor air velocity, human occupancy) recorded during execution of these calibration periods to derive correlations between detection capabilities of the air sampler 104 in the space and environmental conditions within the space.

For example, during each calibration period, in a set of calibration periods for a space, the system can: trigger collection of a bioaerosol sample by the air sampler 104; trigger release of a tracer test load by the dispenser 102; and collect a set of environmental data (e.g., an average air temperature, an average humidity level, a time of day, an average indoor air velocity, an average human occupancy). Then, for each calibration period, in the set of calibration periods, the system can: access a detected barcode level in the bioaerosol sample collected by the air sampler 104; access a true barcode level contained in the tracer test load dispensed by the dispenser 102; derive a calibration factor, in a set of calibration factors, for the space based on a difference between the detected barcode level and the true barcode level; and associate the calibration factor with the set of environmental data collected during the corresponding calibration period. The system can then compile each calibration factor, in the set of calibration factors, associated with the corresponding set of environmental data, into a calibration model for this space defining calibration factor as a function of environmental conditions in this space.

Later, during a live period succeeding the set of calibration periods in this space, the system can leverage this calibration model to calculate a corrected calibration factor for the live period based on environmental conditions in the space during the live period. In particular, during the live period, the system can: trigger collection of a first bioaerosol sample by the air sampler 104 in the space; and collect a first set of environmental data for the space. The system can then: access a detected pathogen level of a pathogen in the bioaerosol sample; calculate a corrected calibration factor for the live period based on the first set of environmental data and the calibration model; and calculate a true pathogen level of the pathogen in the space during the live period based on the detected pathogen load and the corrected calibration factor. Therefore, the system can calculate a unique calibration factor (i.e., corrected calibration factor) for each bioaerosol sample collected in the space based on environmental conditions in this space during collection of the sample. The system can thus account for changes in pathogen detectability within the space due to changes in various environmental conditions within the space.

In another variation, the system can construct a calibration model for the space as a function of pathogen characteristics. In particular, the system can: access characteristics—such as size, functionality, behaviors, etc.—of a set of pathogens defined for the space; derive correlation factors for a corpus of tracer molecules (e.g., barcodes and/or fluorescent material) configured to exhibit characteristics resembling characteristics of the set of pathogens; and derive correlations between detection capabilities of the air sampler 104 in the space and characteristics of the set of pathogens and/or tracer molecules.

For example, during each calibration period, in a set of calibration periods for a space, the system can: trigger collection of a bioaerosol sample by the air sampler 104; trigger release of a tracer test load—containing tracer molecules exhibiting a range of sizes, functionalities, behaviors, etc.—by the dispenser 102; and, for each type of tracer molecule contained in the tracer test load, access a set of characteristics of the tracer molecule. Then, for each calibration period, in the set of calibration periods, and for each type of tracer molecule contained in the tracer test load, the system can: access a detected tracer level (e.g., barcode and/or fluorescence level) in the bioaerosol sample collected by the air sampler 104; access a true tracer level contained in the tracer test load dispensed by the dispenser 102; derive a calibration factor, in a set of calibration factors, for the space based on a difference between the detected tracer level and the true tracer level; and associate the calibration factor with the set of characteristics of the type of tracer molecule. The system can then compile each calibration factor, in the set of calibration factors, associated with the corresponding set of characteristics, into a calibration model for this space defining calibration factor as a function of pathogen characteristics in this space. Later, during a live period succeeding the set of calibration periods in this space, the system can leverage this calibration model to calculate a corrected calibration factor for the live period based on characteristics of pathogens detected in the space during the live period.

11. Calibration: Fluorescent Tracer Molecules

Additionally and/or alternatively, in one variation, the system can run evaluations to calibrate and confirm functionality of the dispenser 102 and/or air sampler 104 based on detection of fluorescent material (e.g., fluorescent tracer molecules) contained in one or more tracer test loads dispensed by the dispenser 102 during the calibration period.

In particular, in this variation, during a calibration period for an environment (e.g., containing the air sampler 104 and the dispenser 102), the system can: trigger collection of an initial bioaerosol sample over an initial sampling period of a fixed duration by the air sampler 104 located in the environment; and, during the first sampling period, trigger dispensation of a first tracer test load by the dispenser 102 located in the environment, the first tracer test load including fluorescent material in solution; access a first detected fluorescence level of fluorescent material detected in air collected by the air sampler 104; access a first true fluorescence level of fluorescent material contained in the first tracer test load; and derive a calibration factor for fluorescent material in the environment based on a difference between the first detected fluorescence level and the first true fluorescence level. The system can then store this calibration factor (or "fluorescence calibration factor") in the calibration profile for the space containing the air sampler 104 and the dispenser 102.

Further, in this variation, during a live period succeeding the calibration period, the system can: trigger collection of a first bioaerosol sample over a first sampling period of the fixed duration by the air sampler 104; access a first detected pathogen level of a first pathogen, in a set of pathogens, detected in the first bioaerosol sample; and predict a first pathogen level of the first pathogen in the first bioaerosol sample based on the first detected pathogen level and the first calibration factor. The system can thus similarly leverage this calibration factor to predict actual (or "true") pathogen levels of various pathogens present in the space based on detected pathogen levels of these pathogens in bioaerosol samples collected by the air sampler 104.

In this variation, the system can similarly derive: a single calibration factor for all fluorescent material released by the dispenser 102 based on a total amount of fluorescence (e.g., an intensity of fluorescence, a quantity of fluorescent molecules or particles) detected at the air sampler 104; a unique calibration factor for each type of fluorescent material—such as different types of fluorescent molecules (e.g., red, yellow, or green fluorescent molecules), fluorescent molecules of different sizes, and/or fluorescent molecules exhibiting different fluorescent properties (e.g., fluorescing at a particular intensity and/or within a particular wavelength range)—released by the dispenser 102; and/or a unique calibration factor for fluorescent material at each location of the dispenser 102($s$) in the space.

11.1 Calibration: Barcodes+Fluorescent Material

In one implementation, the dispenser 102 can release tracer test loads containing tracer molecules including both barcodes (or "DNA barcodes") and fluorescent material. In this implementation, the system can leverage dispensation of a known quantity of barcodes and a known quantity of fluorescent material in a tracer test load released by the dispenser 102 into an environment (or "space") to: derive a calibration factor (or "barcode calibration factor) for barcode levels in the environment based on detected barcode levels in a bioaerosol sample collected by the air sampler 104; and derive a calibration factor (or "fluorescence calibration factor) for fluorescence levels in the environment based on detected fluorescence levels at the air sampler 104, such as via detection of fluorescent aerosols in air flowing through the tunnel 152 of the air sampler 104 and/or present in the bioaerosol sample collected by the air sampler 104.

The system can then derive a conversion model (e.g., a set of conversion factors)—such as a scalar and/or a timeseries of scalars—linking proportions of fluorescent material detected at the air sampler 104 to proportions of barcodes detected in bioaerosol samples collected by the air sampler 104, thereby enabling prediction of barcode levels based on detected fluorescence levels and/or enabling prediction of fluorescence levels based on detected barcode levels. In particular, because detected barcode levels (or "detected amounts of barcodes") — such as collected via genetic analysis (e.g., genetic testing and/or sequencing) of bioaerosol samples collected by the air sampler 104—may be more accurate and/or exhibit less variability than detected fluorescence levels (or "detected amounts of fluorescence" and/or "detected amounts of fluorescent material") — such as collected via detection of fluorescence in air flowing through the air sampler 104 in images (e.g., fluorescence spectra) captured by a set of sensors (e.g., an optical sensor) installed in the air sampler 104—the system can leverage detected barcode levels to calibrate or normalize detected fluorescence levels.

For example, the system can: trigger collection of a bioaerosol sample by the air sampler 104 over a sampling period of a fixed duration (e.g., 1 minute, 10 minutes, 1 hour, 24 hours); during the sampling period, trigger release of a tracer test load containing a known amount of barcodes (e.g., a known barcode level) and a known amount of fluorescent material (e.g., a known fluorescence level); access a detected amount of barcodes (e.g., a detected barcode level) in the bioaerosol sample, such as detected via a genetic detector or a genetic sequencer in the air sampler 104 and/or at a remote facility; access a detected amount of fluorescent material (e.g., a detected fluorescence level) detected in the air sampler 104 (e.g., travelling through the tunnel 152 and/or collected in the bioaerosol sample on the collector plate), such as detected via an optical sensor installed in the air sampler 104 (e.g., within the tunnel 152, proximal the collector plate, and/or in the sampler cartridge 160); derive a barcode calibration factor—representing a proportion of barcodes release in the space and collected by the air sampler 104 during the sampling period—based on the known amount of barcodes and the detected amount of barcodes; and derive a fluorescence calibration factor—representing a proportion of fluorescent material released in the space and detected and/or collected by the air sampler 104 during the sampling period—based on the known amount of fluorescent material and the detected amount of fluorescent material.

Then, based on the barcode calibration factor and the fluorescence calibration factor, the system can derive a conversion model—such as a conversion factor or scalar (e.g., fixed or represented as a function of time, type of tracer molecule, and/or environmental data)—configured to normalize detected amounts of fluorescence (e.g., detected fluorescence levels) detected at the air sampler 104 in the space. The system can thus leverage higher-resolution barcode data collected during this calibration period—such as collected via specific genetic testing and/or complete genetic sequencing of bioaerosol samples collected by the air sampler 104—to normalize, confirm, and/or rectify lower-resolution fluorescence data collected during this calibration period and/or during a live period succeeding the calibration period. Later, during a live period succeeding the calibration period, the system can thus combine low-resolution, high-frequency time series of fluorescence levels detected in the environment with higher-resolution, lower-frequency time series of barcode levels detected in the environment.

Alternatively, in another implementation, the dispenser 102 can release tracer test loads containing tracer molecules including only fluorescent material. In this implementation, the system can derive a calibration factor(s) for fluorescent material in the space as described above.

12. Aerosol Flow Metrics

In one implementation, the system can leverage detection of tracer molecules—released by a particular dispenser 102, in a set of dispensers 102, and detected in air flowing through the air sampler 104—to derive a set of aerosol flow metrics—such as aerosol clearance rate, exposure reduction rate, velocity of aerosol flow, direction of aerosol flow representing movement of aerosols, time-to-detection of aerosols, detectability of aerosols, etc.—representing movement of aerosols (e.g., bioaerosols generally, microbes, pathogens, and/or tracer molecules) in the environment For example, the system can: trigger collection of a bioaerosol sample over a sampling period (e.g., of a fixed or target duration) by the air sampler 104 installed in the environment; during the first sampling period, trigger dispensation of a tracer test load by a first dispenser 102, in a set of dispensers 102, installed in the environment, the tracer test load including tracer molecules (e.g., barcodes and/or fluorescent material) in solution; access a detected amount of tracer molecules present in the bioaerosol sample; access a true amount of tracer molecules present in the tracer test load; and derive a calibration factor, in a set of calibration factors, for the environment based on a difference between the detected amount of tracer molecules and the true amount of tracer molecules. Then, based on the set of calibration factors, the system can deriving a set of aerosol flow metrics—such as detectability of aerosols, a clearance rate, an exposure reduction rate, time and/or duration to initial detection, and/or a velocity of aerosol flow in a region of the environment including the dispenser 102 and the air sampler 104 and/or in a particular direction extending from the dispenser 102 toward the air sampler 104—representing movement of aerosols in the environment, based on the set of calibration factors.

Further, in this implementation, the system can leverage timeseries tracer data collected in the environment over time (e.g., over multiple calibration periods and/or multiple sampling periods) in combination with tracer data collected from multiple locations within the environment—such as by releasing tracer test loads from multiple dispensers 102 deployed throughout the environment, prompting a user to relocate the dispenser 102 in multiple locations, collecting bioaerosol samples from multiple air samplers 104 deployed throughout the environment, and/or prompting the user to relocate the air sampler 104 in multiple locations—to derive a comprehensive set of aerosol flow metrics—representing movement of aerosols throughout the environment.

For example, the system can: trigger collection of a bioaerosol sample, over a sampling period, by an air sampler 104 installed in a first location within the environment; at a first time during the sampling period, trigger dispensation of a tracer test load by a first dispenser 102, in a set of dispensers 102, installed in a first location in the environment, the tracer test load including a first true amount of tracer molecules of a first type in solution; at approximately the first time, trigger dispensation of a second tracer test load by a second dispenser 102, in the set of dispensers 102, installed in a second location in the environment, the second tracer test load including a second true amount of tracer molecules of a second type in solution; during the first sampling period, at a second time succeeding the first time, triggering dispensation of a third tracer test load by the first dispenser 102, the third tracer test load including a third true amount of tracer molecules of a third type in solution; and at approximately the second time, trigger dispensation of a fourth tracer test load by the second dispenser 102, the fourth tracer test load including a fourth true amount of tracer molecules of a fourth type in solution.

Then, the system can: accessing a first detected amount of tracer molecules of the first type present in the bioaerosol sample; derive a first calibration factor, in a set of calibration factors, based on a first difference between the first detected amount and the first true amount, the first calibration factor associated with the first location and a first time value corresponding to the first time; access a second detected amount of tracer molecules of the second type present in the first bioaerosol sample; derive a second calibration factor, in the set of calibration factors, based on a second difference between the second detected amount and the second true amount, the second calibration factor associated with the second location and the first time value; access a third detected amount of tracer molecules of the third type present in the first bioaerosol sample; derive a third calibration factor, in the set of calibration factors, based on a third difference between the third detected amount and the third true amount, the third calibration factor associated with the first location and a second time value corresponding to the second time; access a fourth detected amount of tracer molecules of the third type present in the first bioaerosol sample; and derive a fourth calibration factor, in the set of calibration factors, based on a fourth difference between the fourth detected amount and the fourth true amount, the fourth calibration factor associated with the second location and the second time value. Then, based on the set of calibration factors—including the first, second, third, and fourth calibration factors, each associated with a particular time value and a particular location in the environment—the system can thus derive a set of aerosol flow metrics (e.g., aerosol clearance rate, exposure reduction rate, velocity of aerosol flow, direction of aerosol flow representing movement of aerosols, time-to-detection of aerosols, detectability of aerosols) representative of aerosol movements in the environment.

Further, the system can similarly leverage these calibration factors—and the set of aerosol flow metrics—to: predict pathogen levels of pathogens in the environment based on detected pathogen levels of pathogens detected in bioaerosol samples collected by the air sampler 104; monitor detectability of aerosols in the environment and/or functionality of the air sampler 104 and/or dispenser 102; detect changes (e.g., environmental changes) in the environment based on changes in detectability and/or changes in these calibration factors over time; and/or characterize risk (e.g., risk of pathogen exposure, risk of pathogen transmission) in regions or subregions of the environment based on aerosol flow metrics derived for these particular regions and/or subregions.

13. Facility Mapping: Bioaerosol Movement

In one implementation, the system can leverage spatial information provided for the space to derive an aerosol flow map representing flow—such as characterized by direction, distance, and/or duration (e.g., from release to detection at a particular location)—of bioaerosol particles in the space. In particular, the system can: access a set of images (e.g., lidar-scanned images) of interior spaces within a facility and captured by an optical sensor (e.g., a lidar sensor); and initialize a facility map—defining a 3D rendering or representation of interior spaces within the facility—based on the set of images. The system can then overlay this facility map with air flow information (e.g., air flow rates, direction and/or speed of air currents) derived for this facility from tracer and/or pathogen data collected in this facility to derive an aerosol flow map specific to this particular facility.

For example, during a calibration period, the system can: access a feed of images—including 360-degree lidar-scanned images of a set of spaces (e.g., an office, a breakroom, a bathroom) within the facility—captured by a lidar sensor deployed to the facility during the calibration period; and derive a 3D rendering (or "3D map") of the facility—including 3D representations of each space in the set of spaces in the facility—based on the feed of images collected during the calibration period.

Further, during the calibration period, the system can: trigger collection of a first bioaerosol sample—over a first sampling period of a fixed duration (e.g., 60 seconds, 10 minutes, 1 hour, 24 hours)—by the air sampler 104 installed in a first location within the facility; during the first sampling period, trigger release of a tracer test load—containing a known amount (e.g., concentration, proportion) of tracer molecules (e.g., DNA barcodes, fluorescent material) in solution—by a first dispenser 102 installed in a second location within the facility; access a first detected amount of tracer molecules in the first bioaerosol sample; characterize a difference between the first detected amount of tracer molecules in the first bioaerosol sample and the known amount of tracer molecules in the tracer test load; and derive a set of air flow metrics (e.g., direction, velocity, clearance rate, exposure reduction rate)—representing characteristics and/or patterns of air flow in the facility, such as related to direction, distance, duration, rate (e.g., distance over time)—for the facility based on the difference, the locations (e.g., the first and second location) of the air sampler 104 and the dispenser 102, and/or a duration between dispensation of the tracer test load and detection of the first detected amount of tracer molecules.

In the preceding example, the system can similarly: trigger collection of a series of bioaerosol samples (e.g., including the first bioaerosol sample)—over multiple sampling periods of the fixed (or a dynamic) duration—collected by one or more air samplers 104 installed at multiple locations within the facility; trigger release of a series of tracer test loads—each test load containing known amounts of tracer molecules in solution—by one or more dispensers 102 installed at multiple locations within the facility; and, for each tracer test load released by a dispenser 102 in the facility, interpret a proportion of tracer molecules—contained in the tracer test load—detected by each air sampler 104 installed in the facility, such as at a particular time and/or over a series of timepoints (e.g., at 1 minute, at 5 minutes, at 10-minutes, at 1 hour, at 24 hours). The system can thus leverage these timeseries tracer data to derive the set of air flow metrics for the facility.

Finally, the system can convert these timeseries tracer data into visual representations (e.g., a vector arrow) configured for insertion on the 3D map of the facility to generate a 3D aerosol flow map for this facility. In particular, in this example, the system can: access a first bioaerosol flow rate—representing distance travelled by bioaerosols over a particular time period—derived from the timeseries of tracer data and corresponding to flow of bioaerosols between the first location in the facility and the second location in the facility; interpret a first direction of flow based on the first location and the second location in the facility; and derive a first air flow vector representing magnitude (e.g., flow rate) of bioaerosols in the first direction between the first location and the second location in the facility. The system can repeat this process for each location tested in the facility and/or for each prominent air flow current detected in the facility—such as corresponding to an air flow rate exceeding a threshold air flow rate defined for the facility—to derive a set of air flow vectors for this facility. The system can then overlay the 3D map of the facility with the set of air flow vectors to generate the 3D aerosol flow map for this facility.

The system can therefore leverage this 3D aerosol flow map to: confirm, modify, normalize, and/or generate bioaerosol flow models configured to predict flow of bioaerosols (e.g., pathogens, barcodes, fluorescent material) in the facility based on facility specifications (e.g., dimensions, barriers, door and/or window locations) and/or environmental characteristics (e.g., HVAC settings, human occupancy) of the facility; identify regions of high and/or low risk (e.g., pathogen transmission risk, pathogen exposure risk) in the facility based on air flow patterns in the facility and represented in 3D aerosol flow map; predict flow, dispersion, and/or spread of bioaerosols (e.g., tracer molecules, pathogens) in this facility; and/or provide a visual representation of bioaerosol movements and/or flow patterns throughout the facility—rather than solely provide raw data, such as timeseries bioaerosol data and/or air flow metrics—to a user or users associated with the facility.

Further, the system can characterize risk—such as a pathogen exposure risk for a particular pathogen and/or group of pathogens and/or a pathogen transmission risk for a particular pathogen and/or group of pathogens—in various regions or subregions of the environment based on the aerosol flow map derived for the environment. For example, for each subregion, in a set of subregions, depicted in the aerosol flow map for the environment, the system can characterize risk (e.g., a first risk value) associated with pathogen exposure in the subregion based on the set of aerosol flow metrics derived for the environment. In this example, the system can then selectively flag subregions in the environment for further investigation by a user associated with the environment based on the interpreted risk in these subregions, such as by such as by prompting the user to investigate the subregion and/or implement a particular mitigation technique configured to reduce risk in the subregion.

Further, the system can leverage the aerosol flow map derived for the environment to predict movement or spread of pathogens throughout the environment based on detection of these pathogens in bioaerosol samples collected by one more air samplers 104 in the environment. For example, the system can trigger collection of a bioaerosol sample, over a sampling period, by the air sampler 104. Then, the system can: access a detected pathogen level of a first pathogen, in a set of pathogens, present in the bioaerosol sample; predict a first pathogen level of the first pathogen in a first location in the environment, during the second sampling period, based on the aerosol flow map and the detected pathogen level; and predict a second pathogen level of the first pathogen in a second location in the environment, during the second sampling period, based on the aerosol flow map and the detected pathogen level. The system can similarly predict risk (e.g., pathogen exposure risk, pathogen transmission risk) at various regions or locations within the environment based on the detected pathogen level and the bioaerosol flow map. In particular, in this example, the system can: predict a first risk score—representing risk of exposure to the first pathogen—for a first region (e.g., containing the first location) in the environment based on the aerosol flow map and the detected pathogen level; and predict a second risk score—representing risk of exposure to the first pathogen—for a second region (e.g., containing the second location) in the environment based on the aerosol flow map and the detected pathogen level.

14. Post-Calibration

During a live period succeeding the calibration period, the system can access the calibration profile—including a set of calibration factors and/or a set of calibration curves—for the space to predict pathogen levels within the space based on detected pathogen levels at the air sampler 104.

Further, in one implementation, the system can be configured to intermittently trigger output of tracer test loads, during the live period, by the dispenser 102 to confirm detection of barcodes in bioaerosol samples collected by the air sampler 104. The system can then leverage results of bioaerosol sample testing to: detect whether an air sampler 104 is functioning properly; detect environmental changes in the space that can affect detectability of barcodes and/or pathogens; and/or to update the calibration profile (e.g., including a set of calibration factors and/or a set of calibration curves) for this space.

For example, during a live period for a space, the system can: trigger collection of a bioaerosol sample by the air sampler 104 during a sampling window of a target duration (e.g., matched to a duration of sampling windows during the calibration period) within the live period; and trigger release of a tracer test load by the dispenser 102 within the sampling window. Then, upon completion of genetic testing for the bioaerosol sample, the system can: access a detected barcode level of barcodes within the tracer test load; access a detected pathogen level of pathogens within the bioaerosol sample; access a calibration factor stored in a calibration profile for this space; and estimate a pathogen level for this bioaerosol sample based on the calibration factor and the detected pathogen level. The system can then: access a true barcode level output by the dispenser 102 during the sampling window; calculate a test factor based on the detected barcode level and the true barcode level; and characterize a deviation between the test factor and the calibration factor. Then, in response to the deviation exceeding a threshold deviation, the system can prompt a user (e.g., via the native application) to investigate the space, such as by: confirming placement (e.g., orientation and location) of the air sampler 104; testing a filter of the air sampler 104 to check operation of the air sampler 104; confirming a set of environmental controls in the space (e.g., occupancy, airflow, whether windows are open or closed); etc. Additionally and/or alternatively, the system can initiate a new calibration period to recalibrate this air sampler 104 to increase accuracy of predicted pathogen levels within the space.

In this implementation, the system can leverage calibration data for the space to identify anomalies in barcode levels during the live period. In particular, the system can detect differences between detected barcode levels and "expected" detected barcode levels (e.g., based on the calibration factor for this space) to identify changes in detectability, such as due to environmental changes within the space. Therefore, the system can minimize errors in predicting changes in pathogen levels in the space which may actually be due to changes in detectability in the space caused by other environmental factors (e.g., air dilution, disinfection, filtration, occupancy, barriers).

14.1 Post Calibration: Barcodes+Fluorescent Material

In one variation—in which the dispenser 102 is configured to receive a dispenser cartridge 130 loaded with fluorescent material and/or barcodes—the system can be configured to intermittently trigger output of tracer test loads—containing tracer molecules including fluorescent material and/or barcodes—by the dispenser 102 during the live period in order to: confirm detection of these tracer molecules in bioaerosol samples collected by the air sampler 104; confirm and/or modify a set of calibration factors derived for these tracer molecules, the dispenser 102, and/or the air sampler 104 during the calibration period; monitor and/or detect changes in bioaerosol flow patterns in the environment, such as due to various environment factors (e.g., temperature, humidity, occupancy); and/or to more accurately predict pathogen levels of pathogens detected in bioaerosol samples collected by the air sampler 104.

In one implementation, the system can be configured to: trigger output of tracer test loads containing fluorescent material—and excluding barcodes—at a relatively high-frequency, such as once-per-minute, once-per-hour, and/or once-per-day; and trigger output of tracer test loads containing barcodes at a relatively low-frequency, such as once-per-day, once-per-week, and/or once-per-month. For example, the system can: trigger dispensation of a first sequence of tracer test loads—each tracer test load, in the first sequence of tracer test loads, containing a known amount of fluorescent material (e.g., configured to fluoresce at a known wavelength)—at a first fixed frequency (e.g., once-per-hour); and trigger dispensation of a second sequence of tracer test loads—each tracer test load, in the second sequence of tracer test loads, containing a known amount of barcodes—at a second fixed frequency (e.g., once-per-week) less than the first fixed frequency.

In the preceding implementation, for each tracer test load dispensed by the dispenser 102, the system can then access detected fluorescence levels and/or detected barcode levels detected in air collected by the air sampler 104 from the space during sampling periods corresponding to output of these tracer test loads. The system can thus combine low-resolution, high-frequency fluorescence levels detected in the space—such as via an optical sensor installed in the air sampler 104 and configured to capture fluorescence spectra of particles collected by the air sampler 104 in (near) real time (e.g., during the sampling period)—with high-resolution, low-frequency barcode levels detected in the space—such as via genetic analysis of bioaerosol samples collected by the air sampler 104—to: rapidly detect changes in detectability of tracer molecules and/or pathogens in the space in (near) real time based on changes in detected fluorescence levels; rectify and/or normalize detected fluorescence levels—which may exhibit higher variability and/or less precision than detected barcode levels—based on the higher-resolution detected barcode levels; and/or confirm, modify, and/or replace calibration factors derived for barcodes and/or fluorescent material in the space over time to more accurately predict pathogen levels of pathogens detected in the space.

For example, the system can: trigger collection of a bioaerosol sample over a sampling period by the air sampler 104; at a first time during the sampling period, trigger dispensation of a first tracer test load containing DNA barcodes and fluorescent material in solution; at a second time succeeding the first time during the sampling period, trigger dispensation of a second tracer test load containing fluorescent material in solution; and, at a third time succeeding the second time during the sampling period, trigger dispensation of a third tracer test load containing fluorescent material in solution. The system can then record a timeseries of fluorescence levels detected at the air sampler 104 during the sampling period and including: a first fluorescence level recorded at a fourth time succeeding the first time; a second fluorescence level recorded at a fifth time succeeding the fourth time; and a third fluorescence level recorded at a sixth time succeeding the fifth time. Then, in response to expiration of the sampling period, the system can: access a detected barcode level of barcodes present in the bioaerosol sample; and rectify the timeseries of fluorescence levels detected at the air sampler 104 based on the detected barcode level to derive a normalized timeseries of fluorescence levels detected at the air sampler 104 during the sampling period.

15. Real-Time Management

In one implementation, the system can enable (near) real-time management of the space based on predicted pathogen levels within the space. In particular, the system can selectively prompt users associated with the space to implement mitigation techniques responsive to detection of pathogens within the space. For example, in response to predicting a pathogen level exceeding a threshold pathogen level, the system can: identify a mitigation technique (e.g., reduced capacity, added barriers, increased air filtration) matched to the pathogen level and/or type of pathogen; and prompt a user associated with the space to implement the mitigation technique.

Similarly, the system can enable (near) real-time management of the space based on detected barcode levels within the space. As described above, the system can identify changes in detectability (e.g., at the air sampler 104) based on changes in a proportion of a true barcode level detected at the air sampler 104 (e.g., based on changes in detected barcode levels). The system can then selectively prompt users associated with the space to implement mitigation techniques responsive to instances of reduced detectability. For example, the system can: access a first detected barcode level of a bioaerosol sample collected during a sampling window within the live period; access a true barcode level of a tracer test load dispensed during the sampling window within the live period; calculate a test factor based on the first detected barcode level and the true barcode level; and access a calibration factor (e.g., stored in the calibration profile) derived during the calibration period. In response to a deviation between the test factor and the calibration factor exceeding a threshold deviation, the system can: access a set of environmental controls corresponding to the space (e.g., via wireless communication with a smart system integrated into the space, uploaded by a user); identify a mitigation technique (e.g., refill the dispenser 102, move the air sampler 104, install a fan, remove a barrier blocking the air sampler 104) configured to improve detectability of pathogens and/or barcodes based on the set of environmental controls; and prompt a user to implement this mitigation technique. The system can suggest additional and/or alternative mitigation techniques to the user over multiple sampling periods to increase detectability at this air sampler 104.

16. Intervention Detection

Additionally, in one implementation, Blocks of the method S100 can be executed by the system to characterize effectiveness of intervention types (e.g., chemical, radioactive, and/or electromagnetic disinfectants) configured to treat pressures (e.g., presence and/or magnitude) of pathogens in the space based on detectability of genetically-modified tracer molecules (e.g., barcodes)—linked to particular intervention types—in collected bioaerosol samples. In particular, the dispenser 102 can be configured to release known volumes of a tracer test load including: a known amount of an unmodified tracer molecule (hereinafter "unmodified barcode") configured to enable calibration of the air sampler 104 and/or genetic sequencer; and a known amount of a modified tracer molecule (hereinafter "modified barcode") corresponding to the unmodified tracer molecule and associated with a particular intervention type (e.g., an aerosol disinfectant, a surface disinfectant, a UV-light disinfectant)—such as genetically modified to exhibit specific, sensitive, and detectable properties responsive to contact with the particular intervention type—configured to mitigate pressures of pathogens, a particular pathogen type, and/or a particular pathogen in the space. The air sampler 104 can then collect a bioaerosol sample—including amounts of unmodified and modified barcodes—from the space.

The system can therefore characterize an applied dosage of a particular intervention, in this particular space, based on the known amount of modified barcodes released by the dispenser 102 and the detected amount of these modified barcodes in the bioaerosol sample captured by the air sampler 104. For example, the system can: calculate a percent reduction between the known amount of a particular barcode released by the dispenser 102 and the detected amount of the particular barcode collected by the air sampler 104; and interpret an applied dosage (or "effective dosage") of the particular intervention in the space based on the percent reduction in amount of the particular barcode in the space. The system can then leverage this detected applied dosage to predict effectiveness of the particular intervention in this space and to suggest intervention types and/or dosages of intervention types for mitigating pressures of pathogens in this space.

Additionally, the system can leverage similarities between barcodes and pathogens (e.g., bacteria, viruses) to mimic flow, dispersion, and/or other characteristics of these pathogens within the space to characterize effectiveness of particular intervention types and/or particular dosages of intervention types in treating specific pathogens and/or specific pathogen types. For example, the dispenser 102 can be configured to release barcodes (e.g., modified and/or unmodified barcodes) exhibiting a range of sizes, such that pathogens of different sizes (e.g., within the range of sizes) can be linked to a particular barcode most representative of these pathogens. The system can then leverage differences between amounts of dispensed modified barcodes and detected modified barcodes of different sizes to evaluate effectiveness of an intervention type and/or current dosage of an intervention type present in the space in mitigating pathogens of different sizes.

The system can therefore leverage detection of modified barcodes to characterize effectiveness of various intervention types for mitigating pressures of all pathogens in this space, pressures of pathogens of a particular pathogen type (e.g., size, hardiness, mobility, virility) in this space, and or pressures of a particular pathogen in this space. Further, the system can suggest intervention types and/or dosages of particular intervention types—tailored to this particular space—to a user (or users) associated with the space to minimize spread of pathogens in the space.

16.1 Unmodified & Modified Tracer Molecules

The dispenser 102 can be configured to output tracer test loads of known volumes and including a known amount (e.g., concentration, quantity) of barcodes including amounts of a set of unmodified barcodes and amounts of a set of modified barcodes (e.g., genetically-modified barcodes). In particular, the dispenser 102 can be configured to output: known amounts of a set of unmodified barcodes configured to enable calibration of the air sampler 104 and/or genetic sequencer in this space; and known amounts of a set of modified barcodes configured to enable detection and/or characterization of various intervention techniques in a particular space.

Generally, each modified barcode, in the set of modified barcodes, is derived from a corresponding unmodified barcode, in the set of unmodified barcodes, such that the modified barcode is a genetically-modified variant of the corresponding unmodified barcode. In particular, barcodes (or "unmodified barcodes") can be genetically modified (e.g., via genetic modifications to DNA oligonucleotide structures of unmodified barcodes) to generate modified barcodes configured to enable detection of a particular intervention in the space and/or enable characterization of the effectiveness of this particular invention in this space. For example, an unmodified barcode—including a sequence of nucleobases (e.g., adenine, cytosine, guanine, thymine, uracil) in a DNA strand of the unmodified barcode—can be genetically modified to generate a modified barcode including a chemically-modified structure in replacement of a particular nucleobase in the sequence of nucleobases in the DNA strand of the unmodified barcode. This chemically-modified structure can be configured to exhibit sensitivity to environmental stressors (e.g., chemical, radioactive, electromagnetic) associated with a particular intervention (e.g., application of UV-light, spraying of chemical disinfectants).

Therefore, the resulting modified barcode can be configured to exhibit sensitivity to a particular intervention or group of interventions—such as exhibiting a known, detectable response (e.g., cleavage of the DNA strand at the chemically-modified structure) responsive to detection of these environmental stressors in the space—thereby enabling detection and/or quantification of the particular intervention in the space. For example, the dispenser 102 can release a tracer test load including a quantity of a modified barcode linked to a UV-light disinfectant, a chemical disinfectant (e.g., alcohols, chlorine compounds, formaldehyde), an electromagnetic disinfectant, and/or a radioactive disinfectant.

In one implementation, the dispenser 102 can be configured to release a tracer test load including: a known quantity of an unmodified barcode dissolved in a buffer solution; and a known quantity of a modified barcode—corresponding to the unmodified barcode and linked to a first intervention type—dissolved in the buffer solution. The dispenser 102 can then release a known volume (e.g., a known, airborne volume) of this tracer test load into the space. Additionally, in another implementation, the dispenser 102 can be configured to receive a sequence of tracer test loads configured to be released over time, such as according to a target frequency. In this implementation, each tracer test load, in the sequence of tracer test loads, can include: a known quantity of an unmodified barcode dissolved in a buffer solution; and a known quantity of a modified barcode—corresponding to the unmodified barcode, linked to a first intervention type, and/or including a "label" linking the modified barcode to the tracer test load—dissolved in the buffer solution. Therefore, in this implementation, by genetically modifying modified barcodes to include labels linking these modified barcodes to a particular tracer test load, in the sequence of tracer test loads, the system can differentiate between barcodes released by the dispenser 102 at different times.

16.2 Intervention Dosage

The system can leverage differences between known, dispensed amounts of modified barcodes released into a space and detected amounts of modified barcodes in bioaerosol samples collected in the space during a sampling period to characterize an actual dosage (or "detected dosage") of a particular invention type active in the space during the sampling period.

For example, the system can trigger the dispenser 102—located in a particular space—to output (i.e., dispense) a tracer test load of a known volume and including: a first known quantity of an unmodified barcode; and a second known quantity of a modified barcode—corresponding to the unmodified barcode (e.g., a genetically-modified variant of the unmodified barcode)—configured to detect presence and/or magnitude (e.g., or "dosage") of a UV-light disinfectant. In particular, in this example, the modified barcode can be genetically-modified such that a DNA strand of the modified barcode is cut—fragmenting the DNA strand—responsive to exposure to UV light. Simultaneously, the system can trigger the air sampler 104—located in the particular space—to collect a bioaerosol sample during a sampling period. Then, upon completion of genetic testing for the bioaerosol sample (e.g., within the air sampler 104), the system can: access a first detected quantity of the unmodified barcode within the bioaerosol sample; and access a second detected quantity of the modified barcode within the bioaerosol sample. The system can then: calculate a sampling calibration factor for the space during this sampling period based on the first detected quantity and the first known quantity of the unmodified barcode; calculate an adjusted detected quantity of the modified barcode based on the second detected quantity of the modified barcode and the sampling calibration factor, such as by calculating a percent reduction in a quantity of the modified barcode from the second known quantity in the tracer test load to the adjusted detected quantity in the bioaerosol sample; and characterize a difference between the adjusted detected quantity and the second known quantity of the modified barcode. The system can then characterize a detected dosage of the UV-light disinfectant in the space during the first sampling period based on the difference.

In one implementation, the system can leverage the detected dosage of a particular intervention type in the space—in combination with a known, applied dosage of the particular intervention type in the space—to characterize effectiveness of this particular intervention type in this space. For example, the system can: access a current, applied dosage (e.g., an amount, frequency, duration, and/or distance) of a first intervention type in the space; derive a detected dosage of the first intervention type— based on a difference between a known, dispensed amount of a first modified barcode in a released tracer test load, associated with the first intervention type, and a detected amount of the first modified barcode in a collected bioaerosol sample—in the space; and characterize effectiveness of the first intervention type in the space based on the applied and detected dosages of the first intervention type.

The system can repeat this process for each intervention type, in a set of intervention types, in order to characterize effectiveness of each of these intervention types in this particular space. For example, the system can characterize: a first effectiveness of 50 percent for an aerosol disinfectant; a second effectiveness of 85 percent for a surface disinfectant; a third effectiveness of 30 percent for a UV-light disinfectant; and a fourth effectiveness of 55 percent for an electromagnetic disinfectant (e.g., an electrostatic sprayer 118). The system can then: rank these intervention types for this particular space based on effectiveness; and selectively suggest intervention types to a user or users associated with the particular space based on these rankings.

16.3 Dosage Profile: Defined Target Dosages for Pathogens

In one implementation, the system can access a dosage profile (e.g., a global dosage profile) including a set of target dosages (e.g., for a particular intervention type) corresponding to a set of pathogens. In particular, for each intervention type, in a set of intervention types, the intervention dosage profile can include a set of target dosages—corresponding to the intervention type—each target dosage, in the set of target dosages, corresponding to a particular pathogen, in the set of pathogens.

For example, the system can access an intervention dosage profile including: a first set of target dosages corresponding to a first intervention type; a second set of target dosages corresponding to a second intervention type; and a third set of target dosages corresponding to a third intervention type. In this example, the first set of target dosages, corresponding to the first intervention type, can include: a first target dosage corresponding to a first pathogen (e.g., SARS COV-2), in a set of pathogens, specified for a particular space; a second target dosage corresponding to a second pathogen (e.g., influenza) in the set of pathogens; and a third target dosage corresponding to a third pathogen (e.g., E. Coli) in the set of pathogens. Similarly, in this example, the second set of target dosages corresponding to the second intervention type can include: a fourth target dosage corresponding to the first pathogen; a fifth target dosage corresponding to the second pathogen; and a sixth target dosage corresponding to the third pathogen. The third set of target dosages can similarly include a seventh, eighth, and ninth target dosage corresponding to the first, second, and third pathogens, respectively.

The system can then: compare a target dosage—for a particular intervention type and a particular pathogen type (e.g., a category of pathogens, a particular pathogen)—to a detected dosage for this particular invention type and in a particular space to characterize effectiveness of the detected dosage of this particular intervention in this space for mitigating pressures (e.g., presence and/or magnitude) of the particular pathogen. For example, the system can trigger the dispenser 102 to release a tracer test load of a known volume and including: a first known quantity of an unmodified barcode; and a second known quantity of a modified barcode corresponding to the unmodified barcode and linked to a chemical disinfectant. Simultaneously, the system can trigger the air sampler 104 to collect a bioaerosol sample. Then, upon completion of genetic testing for the bioaerosol sample, the system can: access a first detected quantity of the unmodified barcode within the bioaerosol sample; and access a second detected quantity of the modified barcode within the bioaerosol sample. The system can then: calculate a sampling calibration factor for the space based on the first detected quantity and the first known quantity of the unmodified barcode; calculate an adjusted detected quantity of the modified barcode based on the second detected quantity of the modified barcode and the sampling calibration factor; characterize a difference between the adjusted detected quantity and the second known quantity of the modified barcode; and characterize a detected dosage of the chemical disinfectant in the space based on the difference.

Then, the system can: access a dosage profile corresponding to the chemical disinfectant in the space and specifying a set of target dosages corresponding to a set of pathogens; access a first target dosage, in the set of target dosages, corresponding to a first pathogen, in the set of pathogens; characterize a first difference between the first target dosage and the detected dosage of the chemical disinfectant in the space; and characterize effectiveness of the detected dosage of the chemical disinfectant for mitigating pressures (e.g., presence and/or magnitude) of the first pathogen in the space based on the first difference. The system can similarly repeat this process for each target dosage, in the set of target dosages, to characterize effectiveness of the detected dosage for mitigating pressures of each pathogen, in the set of pathogens.

The system can thus access a dosage profile including target dosages for specific pathogens, pathogen types (e.g., classification, size, virility, life-span), and/or different concentrations of pathogens. In one implementation, the system can derive a space-specific dosage profile based on pathogen detection in the space over time. Alternatively, in another implementation, the system can access a generic or global dosage profile.

In one variation, the system can predict a target dosage—such as for a particular intervention type for a new pathogen (e.g., not previously included in the dosage profile)—based on similarities between pathogens. For example, for a new pathogen detected in the space—and not included in the dosage profile—the system can access a set of characteristics of the new pathogen, such as: a size of the new pathogen; a genetic profile of the new pathogen; a classification of the new pathogen; etc. The system can then leverage these characteristics to identify similar pathogens, included in the dosage profile, and predict a target dosage for each intervention type (e.g., available in the space) based on target dosages, specified in the dosage profile, for these similar pathogens.

16.4 Dosage Calibration

In one implementation, the system can leverage this detected dosage of a particular intervention type in the space to calibrate applied and/or suggested dosages of a particular intervention type in this space. In particular, the system can leverage known applied dosages of a set of intervention types and detected dosages of these intervention types—such as applied and detected during a calibration period—to derive a set of dosage calibration factors for the space, each dosage calibration factor, in the set of dosage calibration factors, corresponding to a particular intervention type, in the set of intervention types. The system can then leverage this set of dosage calibration factors to predict actual applied dosages of the set of interventions types in the space based on known applied dosages. For example, the system can: access a known applied dosage of the UV-light disinfectant in the space; access a detected dosage of the UV-light disinfectant in the space; and derive a dosage calibration factor for the UV-light disinfectant based on the detected dosage and the known applied dosage.

The system can then leverage this dosage calibration factor to: estimate (future) actual dosages of the UV-light disinfectant in the space based on known applied dosages of the UV-light disinfectant; and/or suggest adjusted dosages of the UV-light disinfectant in the space based on known required dosages of the UV-light disinfectant to treat a particular pathogen or pathogens. For example, in response to receiving confirmation of application of a first intervention type (e.g., application of a chemical disinfectant) at a first applied dosage (e.g., at a particular volume, concentration, frequency) in a space, the system can: access a first dosage calibration factor corresponding to the first intervention type and to this space; estimate an adjusted applied dosage based on the first applied dosage and the first dosage calibration factor; access a first target dosage corresponding to the first intervention type and to a first pathogen in a set of pathogens specified for the space; characterize a first difference between the adjusted applied dosage and the first target dosage; and generate a prompt suggesting modifications to application of the first intervention type in the space based on the first difference.

Additionally, the system can repeat this process for each pathogen, in the set of pathogens, to suggest modifications to dosages of the first intervention type based on each pathogen in the set of pathogens. For example, the system can further: access a second target dosage corresponding to the first intervention type and to a second pathogen in the set of pathogens; and characterize a second difference between the adjusted applied dosage and the second target dosage. In this example, the system can generate a prompt suggesting modifications to application of the first intervention type in the space (e.g., according to an adjusted target dosage) based on the first difference and the second difference in order to sufficiently prevent or mitigate presence of the first and second pathogen in the space.

Additionally and/or alternatively, the system can leverage this dosage calibration factor to suggest space-specific dosages of intervention types responsive to detecting pathogens in this space (e.g., in a bioaerosol sample collected by the air sampler 104). For example, in response to detecting a first pathogen level of a first pathogen in a space, the system can: access a target dosage (e.g., a global target dosage) for a first intervention type linked to the first pathogen and corresponding to the first pathogen level; access a first dosage calibration factor corresponding to the first intervention type and to the space; estimate an adjusted target dosage based on the target dosage and the first calibration factor; and prompt a user associated with the space to implement the first intervention type in the space according to the adjusted target dosage.

16.5 Modified Tracer Molecule: Pathogen-Specific

In one implementation, the dispenser 102 can be configured to release a tracer test load including quantities of a modified barcode corresponding to a particular pathogen and/or pathogen type. In particular, this modified barcode can be genetically modified to exhibit characteristics—such as size, hardiness, mobility—imitating the particular pathogen and/or pathogen type, such that the modified barcode mimics: flow or dispersion of pathogens of the particular pathogen and/or pathogen type within the space; and response of the particular pathogen and/or pathogens of the particular pathogen type to various intervention types. The system can then leverage detected quantities of modified barcodes—associated with particular pathogens and/or pathogen types—to characterize effectiveness of dosages of various intervention types in a space for particular pathogens and/or pathogen types.

For example, the dispenser 102 can be configured to release a tracer test load including: a first quantity of a first modified barcode of a first size corresponding to a first intervention type and associated with a first pathogen type, pathogens of the first pathogen type exhibiting sizes within a first size range including the first size; and a second quantity of a second modified barcode of a second size—greater than the first size—corresponding to the first intervention type and associated with a second pathogen type, pathogens of the second pathogen type exhibiting sizes within a second size range including the second size. Additionally, in this example, the tracer test load can include quantities of unmodified barcodes—corresponding to each modified barcode—in order to calibrate the detected quantity of modified barcodes in the resulting bioaerosol sample collected by the air sampler 104. In particular, in this example, the tracer test load can further include: a third quantity of a first unmodified barcode of the first size and corresponding to the first modified barcode; and a fourth quantity of a second unmodified barcode of the second size and corresponding to the second modified barcode. During or immediately succeeding release of this tracer test load by the dispenser 102, the system can trigger the air sampler 104 to collect a bioaerosol sample from this space. Then, upon completion of genetic testing of the bioaerosol sample, the system can: access a first detected quantity of the first modified barcode in the bioaerosol sample; access a second detected quantity of the second modified barcode in the bioaerosol sample; access a third detected quantity of the first unmodified barcode in the bioaerosol sample; and access a fourth detected quantity of the second unmodified barcode in the bioaerosol sample.

In the preceding example, the system can then: calculate a first sampling calibration factor corresponding to the first pathogen type and based on the third detected quantity of the first unmodified barcode and the third quantity of the first unmodified barcode in the tracer test load; and calculate a second sampling calibration factor corresponding to the second pathogen type and based on the fourth detected quantity of the second unmodified barcode and the fourth quantity of the second unmodified barcode in the tracer test load. Then, the system can: calculate a first adjusted quantity of the first modified barcode based on the first sampling calibration factor and the first detected quantity of the first modified barcode; and calculate a second adjusted quantity of the second modified barcode based on the second sampling calibration factor and the second detected quantity of the second modified barcode. Further, the system can: characterize a first detected dosage of the first intervention type—corresponding to the first pathogen type—based on the first adjusted quantity of the first modified barcode in the bioaerosol sample and the first quantity of the first modified barcode in the tracer test load; and characterize a second detected dosage of the first intervention type—corresponding to the second pathogen type—based on the second adjusted quantity of the second modified barcode in the bioaerosol sample and the second quantity of the second modified barcode in the tracer test load. Finally, the system can: access an applied dosage (e.g., amount, frequency, duration, distance) of the first intervention type; and characterize effectiveness of the first intervention type at the applied dosage for mitigating pressures (e.g., presence and/or magnitude) of pathogens of the first and second pathogen type in this particular space based on differences between the applied dosage and the first and second detected dosages.

16.5.1 Pathogen-Specific Tracer Molecules: Modified Behavioral Properties

In one implementation, the dispenser 102 can be configured to release tracer test loads including quantities of a modified barcode configured to mimic behaviors of a particular pathogen responsive to detection of a particular intervention type. This pathogen-specific modified barcode can be genetically-modified to exhibit a set of detectable characteristics—linking the pathogen-specific modified barcode to the particular pathogen—responsive to contact with a particular intervention type. For example, a modified barcode can be genetically modified to include secondary structures (i.e., RNA secondary structures)—such as a loop in one of the DNA strands of the modified barcode—that enable the modified barcode to exhibit properties specific to a particular pathogen. In another example, the modified barcode can be genetically modified to include a molecule attached to the DNA strand of the modified barcode that enables the modified barcode to exhibit properties specific to the particular pathogen.

In this implementation, the system can leverage the detected dosage of a particular intervention type in the space—in combination with a known, applied dosage of the particular intervention type in the space—to characterize effectiveness of this particular intervention type for a particular pathogen, in a set of pathogens, in this space. The system can repeat this process for each intervention type, in a set of intervention types, and for each pathogen, in the set of pathogens, in order to characterize effectiveness of each of these intervention types for each pathogen in this particular space. For example, the system can characterize: a first effectiveness of a first intervention type (e.g., a chemical aerosol) for treating a first pathogen in a set of pathogens defined for the space; a second effectiveness of the first intervention type for treating a second pathogen in the set of pathogens; and a third effectiveness of the first intervention type for treating a third pathogen in the set of pathogens. Additionally, the system can characterize: a first effectiveness of a second intervention type (e.g., a UV-light disinfectant) for treating the first pathogen in the space; a second effectiveness of the second intervention type for treating the second pathogen in the space; and a third effectiveness of the second intervention type for treating the third pathogen in the space.

Over time (e.g., during and/or after a calibration period for a space), the system can identify intervention types and/or particular dosages of intervention types characterized by high effectiveness (e.g., compared to other intervention types and/or compared to particular dosages of intervention types) in mitigating pressures of specific pathogens in the space. The system can leverage this information to: derive a space-specific and pathogen-specific dosage profile for application of various intervention types in this space; and suggest space- and pathogen-specific dosages of particular intervention types to users associated with the space for preventing and/or mitigating pressures of pathogens in this space. For example, in response to detecting a first pathogen level of a first pathogen in the space in a bioaerosol sample collected by the air sampler 104, the system can: access a dosage profile stored for this particular space; select a first intervention type, in a set of intervention types, for treating the first pathogen level of the first pathogen in the space based on effectiveness of the set of intervention types; generate a prompt suggesting a first dosage—matched to the first pathogen level (e.g., based on the pathogen profile)—of the first intervention type in the space to treat the first pathogen level of the first pathogen; and transmit the prompt to a user associated with the space.

17. Modified Barcode Library: Single Unmodified Tracer Molecule+Multiple Modified Tracer Molecules In one implementation, the dispenser 102 can be configured to dispense a volume of a tracer test load including unmodified barcodes of a first type (e.g., identical unmodified tracer molecules) and modified barcodes—corresponding to unmodified barcodes of the first type—linked to a set of interventions. For example, the dispenser 102 can be configured to release a tracer test load including: a control quantity of an unmodified barcode of a first barcode type (e.g., within a particular size range, configured to detect a particular pathogen); a first quantity of a first modified barcode of the first barcode type and linked to a first intervention (e.g., UV light); a second quantity of a second modified barcode of the first barcode type and linked to a second intervention (e.g., a particular chemical disinfectant); and a third quantity of a third modified barcode of the first barcode type and linked to a third intervention (e.g., an electrostatic sprayer 118). In this example, the system can: trigger collection of a bioaerosol sample by the air sampler 104 during a sampling window of a target duration; and trigger release of the tracer test load by the dispenser 102 within the sampling window. Then, upon completion of genetic testing for the bioaerosol sample (e.g., within the air sampler 104), the system can: access a detected control quantity of the unmodified barcode within the bioaerosol sample; access a first detected quantity of the first unmodified barcode within the bioaerosol sample; access a second detected quantity of the second unmodified barcode within the bioaerosol sample; and access a third detected quantity of the third unmodified barcode within the bioaerosol sample. The system can then: calculate a sampling calibration factor for the space during this sampling window based on the detected control quantity and the control quantity; calculate a first adjusted quantity of the first unmodified barcode within the bioaerosol sample based on the first detected quantity and the calibration factor; calculate a second adjusted quantity of the second unmodified barcode within the bioaerosol sample based on the second detected quantity and the calibration factor; and calculate a third adjusted quantity of the third unmodified barcode within the bioaerosol sample based on the third detected quantity and the calibration factor.

Finally, in the preceding example, the system can: characterize a first detected dosage of the first intervention type in the space based on a first difference between the first adjusted quantity of the first modified barcode in the bioaerosol sample and the first quantity of the first modified barcode dispensed in the tracer test load; characterize a second dosage of the second intervention type in the space based on a second difference between the second adjusted quantity of the second modified barcode in the bioaerosol sample and the second quantity of the second modified barcode dispensed in the tracer test load; and characterize a third dosage of the third intervention in the space based on a third difference between the third adjusted quantity of the third modified barcode in the bioaerosol sample and the third quantity of the third modified barcode dispensed in the tracer test load. The system can therefore derive current detected dosages of each of these intervention types in the space during the sampling window and thus identify which intervention types exhibit high activity (i.e., effectiveness) in this particular space and which intervention types exhibit lower activity in this particular space. The system can leverage these detected dosages to suggest intervention types—exhibiting high activity in this particular space—to a user or users associated with the space in order to prevent and/or mitigate pressures of pathogens in this particular space.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

I claim:

1. A method comprising:
during a calibration period for an environment:
triggering collection of an initial bioaerosol sample over an initial sampling period of a fixed duration by an air sampler located in the environment;
during the first sampling period, triggering dispensation of a first tracer test load by a dispenser located in the environment, the first tracer test load comprising a set of barcodes in solution;
accessing a first detected barcode level of a first barcode, in the set of barcodes, detected in the initial bioaerosol sample;
accessing a first true barcode level of the first barcode present in the first tracer test load; and
deriving a first calibration factor, in a set of calibration factors, for the first barcode in the environment based on a difference between the first detected barcode level and the first true barcode level; and
during a live period succeeding the calibration period:
triggering collection of a first bioaerosol sample over a first sampling period of the fixed duration by the air sampler;
accessing a first detected pathogen level of a first pathogen, in a set of pathogens, detected in the first bioaerosol sample; and
predicting a first pathogen level of the first pathogen in the first bioaerosol sample based on the first detected pathogen level and the first calibration factor.

2. The method of claim 1, further comprising, in response to the first pathogen level exceeding a threshold pathogen level:
selecting a first mitigation technique, in a set of mitigation techniques, configured to reduce the first pathogen level of the first pathogen;
generating a prompt to execute the first mitigation technique in the environment; and
transmitting the prompt to a user associated with the environment.

3. The method of claim 1:
further comprising, during the calibration period:
accessing a second detected barcode level of a second barcode, in the set of barcodes, detected in the first bioaerosol sample;
accessing a second true barcode level of the second barcode present in the first tracer test load; and
deriving a second calibration factor, in the set of calibration factors, for the second barcode in the environment based on a difference between the second detected barcode level and the second true barcode level; and wherein predicting the first pathogen level of the first pathogen in the first bioaerosol sample based on the first detected pathogen level and the first calibration factor comprises:
selecting the first calibration factor, in place of the second calibration factor, based on characteristics of the first pathogen;
predicting the first pathogen level of the first pathogen in the first bioaerosol sample based on the first detected pathogen level and the first calibration factor.

4. The method of claim 3, wherein selecting the first calibration factor, in place of the second calibration factor, based on characteristics of the first pathogen comprises:
accessing a first set of characteristics of the first pathogen;
accessing a calibration model linking characteristics of pathogens in the environment to the set of calibration factors based on characteristics of barcodes in the set of barcodes; and
selecting the first calibration factor, in place of the second calibration factor, based on the first set of characteristics and the calibration model.

5. The method of claim 3, further comprising, during the live period:
accessing a second detected pathogen level of a second pathogen, in the set of pathogens, detected in the second bioaerosol sample;
selecting the second calibration factor, in place of the first calibration factor, based on characteristics of the second pathogen; and
predicting a second pathogen level of the second pathogen in the first bioaerosol sample based on the second detected pathogen level and the second calibration factor.

6. The method of claim 1:
wherein triggering dispensation of the first tracer test load comprising the set of DNA barcodes in solution comprises triggering dispensation of the first tracer test load comprising the set of DNA barcodes, each DNA barcode comprising:
a unique identifier, in a set of unique identifiers, associated with the DNA barcode and distinct from each other unique identifier in the set of unique identifiers; and
a group identifier associated with the set of DNA barcodes and common to barcodes in the set of DNA barcodes; and
wherein accessing the first detected barcode level of the first barcode comprises:
accessing a quantity of unique identifiers detected in the first bioaerosol sample; and
interpreting the first detected barcode level of the first barcode based on the quantity of unique identifiers.

7. The method of claim 1:
wherein triggering dispensation of the first tracer test load comprising the set of barcodes in solution comprises triggering dispensation of the first tracer test load comprising the set of barcodes and fluorescent material in solution;
wherein deriving the first calibration factor for the first barcode comprises deriving a first barcode calibration factor, in a set of barcode calibration factors, for the first barcode; and
further comprising:
accessing a first detected fluorescence level of fluorescent material detected in the first bioaerosol sample;

accessing a first true fluorescence level of fluorescent material present in the first fluorescence test load;

deriving a first fluorescence calibration factor, in a set of fluorescence calibration factors, for fluorescent material in the environment based on a difference between the detected fluorescence level and the first true fluorescence level; and deriving a conversion factor based on the first barcode calibration factor and the first fluorescence calibration factor.

8. The method of claim 7, further comprising, during the live period:

triggering dispensation of a second tracer test load by the dispenser located in the environment, the second tracer test load comprising fluorescent material in solution;

accessing a second detected fluorescence level of fluorescent material present in the first bioaerosol sample;

estimating a corrected detected fluorescence level of fluorescent material present in the first bioaerosol sample based on the second detected fluorescence level and the conversion factor; and in response to the corrected detected fluorescence level falling below a threshold fluorescence level defined for the environment during the first sampling period, flagging the environment for further investigation by a user associated with the environment.

9. The method of claim 1, further comprising:

during the calibration period:

triggering collection of a second bioaerosol sample over a second sampling period of the fixed duration by the air sampler;

during the second sampling period, triggering dispensation of a second tracer test load by the dispenser, the second tracer test load comprising a second set of barcodes in solution;

accessing a second detected barcode level of the first barcode, in the second set of barcodes, detected in the second bioaerosol sample;

accessing a second true barcode level of the first barcode present in the second tracer test load;

deriving a second calibration factor, in the set of calibration factors, for the first barcode in the environment based on a second difference between the second detected barcode level and the second true barcode level;

accessing a first set of environmental data recorded for the environment during the initial sampling period;

accessing a second set of environmental data recorded for the environment during the second sampling period; and deriving a calibration model linking environmental data to the set of calibration factors in the environment based on the first calibration factor, the first set of environmental data, the second calibration factor, and the second set of environmental data; and wherein predicting the first pathogen level of the first pathogen in the first bioaerosol sample based on the first detected pathogen level and the first calibration factor comprises:

accessing a third set of environmental data recorded for the environment during the first sampling period;

selecting the first calibration factor, in place of the second calibration factor, based on the third set of environmental data and the calibration model; and predicting the first pathogen level of the first pathogen in the first bioaerosol sample based on the first detected pathogen level and the first calibration factor.

10. The method of claim 1:

wherein triggering dispensation of the first tracer test load by the dispenser located in the environment comprises triggering dispensation of the first tracer test load by a first dispenser installed in a first location in the environment, the first tracer load comprising the first barcode in solution;

wherein deriving the first calibration factor for the first barcode in the environment comprises deriving the first calibration factor for the first barcode dispensed from the first location in the environment; and further comprising, during the calibration period:

during the first sampling period, triggering dispensation of a second tracer test load by a second dispenser installed in a second location in the environment, the second tracer test load comprising a second barcode in solution;

accessing a second detected barcode level of the second barcode detected in the initial bioaerosol sample;

accessing a second true barcode level of the second barcode present in the second tracer test load; and deriving a second calibration factor, in the set of calibration factors, for the second barcode, dispensed from the second location, based on a difference between the second detected barcode level and the second true barcode level;

characterizing aerosol movement between the first location and a location of the air sampler based on the first calibration factor; and characterizing aerosol movement between the second location and the location of the air sampler based on the second calibration factor.

11. The method of claim 1:

wherein triggering collection of the first bioaerosol sample by the air sampler comprises triggering collection of the first bioaerosol sample by the air sampler comprising:

a sampler housing defining an air inlet and an air outlet;

a tunnel arranged within the housing and extending between the air inlet and the air outlet;

a charge electrode arranged within the tunnel proximal the inlet;

a cartridge receptacle arranged proximal the outlet within the housing and comprising a cartridge terminal;

a power supply configured to drive a voltage between the charge electrode and the cartridge terminal; and a sampler cartridge comprising:

a substrate;

a collector plate arranged on the substrate and configured to collect charged bioaerosols moving through the tunnel; and a connector configured to transiently engage the cartridge receptacle to locate the substrate and the collector plate within the tunnel and electrically couple the collector plate to the cartridge terminal; and wherein triggering release of the first tracer test load by the dispenser comprises triggering release of the first tracer test load by the dispenser comprising:

a dispenser cartridge comprising DNA barcodes in solution;

a dispenser communication module configured to receive commands for operation of the dispenser; and an actuator configured to release a solution dose from the dispenser cartridge based on a command received by the dispenser communication module.

12. A method comprising:

during a calibration period for an environment:
triggering collection of an initial bioaerosol sample over an initial sampling period of a fixed duration by an air sampler located in the environment;
during the first sampling period, triggering dispensation of a first tracer test load by a dispenser located in the environment, the first tracer test load comprising fluorescent material in solution;
accessing a first detected fluorescence level of fluorescent material detected in air collected by the air sampler;
accessing a first true fluorescence level of fluorescent material present in the first tracer test load; and
deriving a fluorescence calibration factor for fluorescent material in the environment based on a difference between the first detected fluorescence level and the first true fluorescence level; and during a live period succeeding the calibration period:
triggering collection of a first bioaerosol sample over a first sampling period of the fixed duration by the air sampler;
accessing a first detected pathogen level of a first pathogen, in a set of pathogens, detected in the first bioaerosol sample; and
predicting a first pathogen level of the first pathogen in the first bioaerosol sample based on the first detected pathogen level and the first calibration factor.

13. The method of claim 12:
wherein triggering dispensation of the first tracer test load by the dispenser comprises triggering dispensation of the first tracer test load by a first dispenser installed in a first location, the first tracer test load comprising fluorescent material of a first type in solution;
wherein accessing the first detected fluorescence level of fluorescent material comprises accessing the first detected fluorescence level of fluorescent material of the first type;
wherein accessing the first true fluorescence level of fluorescent material comprises accessing the first true fluorescence level of fluorescent material of the first type;
wherein deriving the fluorescence calibration factor for fluorescent material based on the difference between the first detected fluorescence level and the first true fluorescence level comprises deriving a first fluorescence calibration factor for fluorescent material dispensed at the first location based on a first difference between the first detected fluorescence level and the first true fluorescence level; and
further comprising:
triggering dispensation of a second tracer test load by a second dispenser installed in a second location, the second tracer test load comprising fluorescent material of a second type in solution;
accessing a second detected fluorescence level of fluorescent material of the second type detected in air collected by the air sampler type;
accessing a second true fluorescence level of fluorescent material of the second type present in the second tracer test load; and
deriving a second fluorescence calibration factor for fluorescent material dispensed at the second location based on a second difference between the second detected fluorescence level and the second true fluorescence level.

14. The method of claim 12:
wherein triggering dispensation of the first tracer test load comprising fluorescent material in solution comprises triggering dispensation of the first tracer test load comprising fluorescent material and DNA barcodes in solution; and
further comprising, during the calibration period:
accessing a first detected barcode level of DNA barcodes detected in the initial bioaerosol sample;
accessing a first true barcode level of DNA barcodes present in the first tracer test load;
deriving a barcode calibration factor for DNA barcodes in the environment based on a difference between the first detected barcode level and the first true barcode level; and
deriving a fluorescence conversion factor based on a difference between the barcode calibration factor and the fluorescence calibration factor.

15. The method of claim 14, further comprising, during the live period:
triggering collection of a second bioaerosol sample over a second sampling period of the fixed duration by the air sampler;
during the second sampling period, triggering dispensation of a second tracer test load by the dispenser, the second tracer test load comprising fluorescent material and DNA barcodes in solution;
accessing a timeseries of detected fluorescence levels of fluorescent material detected in air flowing through the air sampler during the second sampling period;
correcting the timeseries of detected fluorescence levels based on the fluorescence conversion factor;
accessing a second detected barcode level of DNA barcodes detected in the second bioaerosol sample; and
normalizing the timeseries of detected fluorescence levels based on the second detected barcode level.

16. The method of claim 12, further comprising, during the live period:
at a first time, triggering dispensation of a second tracer test load by the dispenser, the second tracer test load comprising fluorescent material in solution;
accessing a second detected fluorescence level of fluorescent material detected in air collected by the air sampler at a second time succeeding the first time; and
in response to the second detected fluorescence level falling below a threshold fluorescence level, flagging the environment for further investigation.

17. The method of claim 12:
wherein accessing the first detected fluorescence level of fluorescent material detected in air collected by the air sampler comprises accessing the first detected fluorescence level of fluorescent material detected in air collected by the air sampler at a first time during the initial sampling period; and
further comprising, during the calibration period:
accessing a second detected fluorescence level of fluorescent material detected in air collected by the air sampler at a second time succeeding the first time during the initial sampling period;
deriving a second fluorescence calibration factor for fluorescent material in the environment based on a second difference between the second detected fluorescence level and the first true fluorescence level;
associating the first fluorescence calibration factor with a first time value corresponding to the first time;
associating the second fluorescence calibration factor with a second time value corresponding to the second time; and
deriving a calibration curve for fluorescent material in the environment based on the first calibration factor, the first time value, the second calibration factor, and the second time value.

18. The method of claim 17, further comprising, during the live period:
at a third time, triggering dispensation of a second tracer test load by the dispenser, the second tracer test load comprising fluorescent material exhibiting a second true fluorescence level;
estimating a predicted fluorescence level of fluorescent material detected by the air sampler at a fourth time succeeding the third time based on the calibration curve and the second true fluorescence level;
accessing a second detected fluorescence level of fluorescent material detected in air collected by the air sampler at approximately the fourth time;
characterizing a difference between the predicted fluorescence level and the second detected fluorescence level; and
in response to the difference exceeding a threshold difference, flagging the environment for further investigation.

19. A method comprising:
during a calibration period:
triggering collection of a first bioaerosol sample, over a first sampling period, by an air sampler installed in an environment;
during the first sampling period:
at a first time, triggering dispensation of a first tracer test sample by a first dispenser installed in a first location in the environment, the first tracer test sample comprising a first true tracer level of tracer molecules of a first type in solution; and
at approximately the first time, triggering dispensation of a second tracer test sample by a second dispenser installed in a second location in the environment, the second tracer test sample comprising a second true tracer level of tracer molecules of a second type in solution;
accessing a first detected level of tracer molecules of the first type present in the bioaerosol sample;
accessing a second detected level of tracer molecules of the second type present in the bioaerosol sample;
deriving a first calibration factor, in a set of calibration factors, for tracer molecules dispensed from the first dispenser at the first location based on a first difference between the first detected tracer level and the first true tracer level;
deriving a second calibration factor, in the set of calibration factors, for tracer molecules dispensed from the second dispenser at the second location based on a second difference between the second detected tracer level and the second true tracer level; and
interpreting a set of aerosol flow patterns in the environment based on the set of calibration factors; and
during a live period succeeding the calibration period:
triggering collection of a second bioaerosol sample, over a second sampling period, by the air sampler; and
in response to detecting a first pathogen level of a first pathogen, in a set of pathogens, present in the second bioaerosol sample, predicting a pathogen level gradient of the first pathogen in the environment based on the first pathogen level and the set of aerosol flow patterns.

20. The method of claim 19:
wherein triggering dispensation of the first tracer test sample comprising the first true tracer level of tracer molecules of the first type in solution comprises triggering dispensation of the first tracer test sample comprising the first true tracer level of tracer molecules of the first type in solution, tracer molecules of the first type comprising a first set of DNA barcodes, each DNA barcode, in the first set of DNA barcodes, comprising:
a unique identifier, in a first set of unique identifiers, associated with the DNA barcode and distinct from each other unique identifier in the first set of unique identifiers; and
a first group identifier associated with the first set of DNA barcodes and common to DNA barcodes in the first set of DNA barcodes; and
wherein triggering dispensation of the second tracer test sample comprising the second true tracer level of tracer molecules of the second type in solution comprises triggering dispensation of the second tracer test sample comprising the second true tracer level of tracer molecules of the second type in solution, tracer molecules of the second type comprising a second set of DNA barcodes, each DNA barcode, in the second set of DNA barcodes, comprising:
a unique identifier, in a second set of unique identifiers, associated with the DNA barcode and distinct from each other unique identifier in the second set of unique identifiers; and
a second group identifier associated with the second set of DNA barcodes and common to DNA barcodes in the second set of DNA barcodes.

* * * * *